(12) United States Patent
Biber et al.

(10) Patent No.: US 11,199,598 B2
(45) Date of Patent: Dec. 14, 2021

(54) MRI SCANNER WITH ACTIVE INTERFERENCE SUPPRESSION AND INTERFERENCE SUPPRESSION METHOD FOR AN MRI SCANNER

(71) Applicant: Siemens Healthcare GmbH, Erlangen (DE)

(72) Inventors: Stephan Biber, Erlangen (DE); Ian Edward Nichols, Eastleigh (GB); David James Sadler, Eastleigh (GB); David Grodzki, Erlangen (DE); Markus Vester, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/753,796

(22) PCT Filed: Oct. 2, 2018

(86) PCT No.: PCT/EP2018/076746
§ 371 (c)(1),
(2) Date: Apr. 5, 2020

(87) PCT Pub. No.: WO2019/068687
PCT Pub. Date: Apr. 11, 2019

(65) Prior Publication Data
US 2020/0249292 A1 Aug. 6, 2020

(30) Foreign Application Priority Data
Oct. 5, 2017 (EP) .................................... 17194969

(51) Int. Cl.
*G01R 33/36* (2006.01)
*A61B 5/055* (2006.01)
(Continued)

(52) U.S. Cl.
CPC .......... *G01R 33/3692* (2013.01); *A61B 5/055* (2013.01); *G01R 33/3614* (2013.01);
(Continued)

(58) Field of Classification Search
CPC ............ G01R 33/3692; G01R 33/3614; G01R 33/3635; G01R 33/3854; G01R 33/422;
(Continued)

(56) References Cited

U.S. PATENT DOCUMENTS 5,125,108 A * 6/1992 Talwar .................... H04B 1/126
343/853
8,258,788 B2 * 9/2012 Hulbert .............. G01R 33/3692
324/318
(Continued)

FOREIGN PATENT DOCUMENTS

DE 102014207843 A1 10/2015
EP 3467531 A1 4/2019
(Continued)

OTHER PUBLICATIONS

Braune, Joerg: "Nonlinear behavior and intermodulation"; Nov. 2005. pp. 1-3.
(Continued)

*Primary Examiner* — G. M. A Hyder
(74) *Attorney, Agent, or Firm* — Lempia Summerfield Katz LLC

(57) ABSTRACT

An MRI scanner and a method for operation of the MRI scanner are provided. The MRI scanner has a first receiving antenna for receiving a magnetic resonance signal from a patient in a patient tunnel, a second receiving antenna for receiving a signal having the Larmor frequency of the magnetic resonance signal, and a receiver. The second receiving antenna is located outside of the patient tunnel or near an opening thereof. The receiver has a signal connec-
(Continued)

tion to the first receiving antenna and the second receiving antenna and is configured to suppress an interference signal by the second receiving antenna in the magnetic resonance signal received by the first receiving antenna.

43 Claims, 7 Drawing Sheets

(51) Int. Cl.

| | | |
|---|---|---|
| *G01R 33/385* | (2006.01) | |
| *G01R 33/422* | (2006.01) | |
| *G01R 33/48* | (2006.01) | |
| *G01R 33/483* | (2006.01) | |
| *G01R 33/54* | (2006.01) | |
| *G01R 33/56* | (2006.01) | |
| *G01R 33/565* | (2006.01) | |
| *G01R 33/58* | (2006.01) | |

(52) U.S. Cl.
CPC ..... *G01R 33/3635* (2013.01); *G01R 33/3854* (2013.01); *G01R 33/422* (2013.01); *G01R 33/4818* (2013.01); *G01R 33/4833* (2013.01); *G01R 33/543* (2013.01); *G01R 33/5608* (2013.01); *G01R 33/5659* (2013.01); *G01R 33/583* (2013.01)

(58) Field of Classification Search
CPC ............ G01R 33/4818; G01R 33/4833; G01R 33/543; G01R 33/5608; G01R 33/5659; G01R 33/583; A61B 5/055
See application file for complete search history.

(56) References Cited

U.S. PATENT DOCUMENTS

| | | | |
|---|---|---|---|
| 2008/0048658 A1* | 2/2008 | Hushek | ................ G01R 33/422 324/309 |
| 2014/0155732 A1 | 6/2014 | Patz | |
| 2015/0309131 A1 | 10/2015 | Rehner | |
| 2017/0108569 A1* | 4/2017 | Harvey | ................ G01R 33/422 |
| 2019/0146048 A1 | 5/2019 | Kannengiesser | |

FOREIGN PATENT DOCUMENTS

| | | |
|---|---|---|
| WO | WO2013016639 A1 | 1/2013 |
| WO | WO2015150236 A1 | 10/2015 |

OTHER PUBLICATIONS

European Search Report for European Application No. 17194969.6-1022 dated Apr. 20, 2018.
International Search Report and the Written Opinion for International Patent Application PCT/EP2018/076746 dated Apr. 15, 2019.
Kessy, Agnan, et al. "Optimal whitening and decorrelation." The American Statistician 72.4 (Dec. 2016): 1-14.
Roke Manor Research Ltd: "Dynamic Cancellation Performance: Moving Interference Source: Experiment 9"; 72/18/N/147/R; pp. 84-92 (of 319).
Tian Bao-Feng et al: "Removal method of industrial frequency harmonics in nuclear magnetic resonance signal based on adaptive filter", Database accession No. 11090128 ; & Journal of Jilin University (Information Science Edition); Jilin University China. May 2009.
Wikipedia: "ISM-Band"; Jan. 2018; https://en.wikipedia.org/wiki/ISM_band. pp. 1-7.

* cited by examiner

MRI SCANNER WITH ACTIVE INTERFERENCE SUPPRESSION AND INTERFERENCE SUPPRESSION METHOD FOR AN MRI SCANNER

This application is the National Stage of International Application No. PCT/EP2018/076746, filed Oct. 2, 2018, which claims the benefit of European Patent Application No. EP 17194969.6, filed Oct. 5, 2017. The entire contents of these documents are hereby incorporated herein by reference.

BACKGROUND

The present embodiments relate to an active interference suppression method in a magnetic resonance imaging (MRI) scanner and also to an MRI scanner with a receiver.

MRI scanners are imaging facilities that, for imaging an examination object, align nuclear spins of the examination object with a strong external magnetic field and excite the nuclear spins with a magnetic alternating field for precession about this alignment. The precession or return of the spins from this excited state back into a state with lower energy creates, as a response, a magnetic alternating field that is received via antennas.

A spatial encoding is impressed on the signals with the aid of magnetic gradient fields, which subsequently makes it possible to assign the received signal to a volume element. The received signal is then evaluated, and a three-dimensional imaging representation of the examination object is provided. To receive the signal, local receiving antennas (e.g., local coils) that may be used to achieve a better signal-to-noise ratio are arranged directly on the examination object. The receiving antennas may also be built into a patient couch.

MRI scanners require radio frequency screening in two respects. Frequency pulses with powers in the kilowatt range are generated to excite the nuclear spins, which are only partly absorbed in the patient. Radio waves that leave the patient tunnel are radiated out into the room and are therefore to be screened out to adhere to emission limit values.

Conversely, the magnetic resonance signals to be received for the imaging are extremely weak. In order to obtain a sufficient signal-to-noise ratio (SNR), a screening out of external interference signals is to be provided.

In the prior art, complex screening cabins are therefore installed around an MRI scanner in order to reduce both emissions and also immissions.

A knee coil with local screening is known from publication DE 102014207843.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an outlay for screening may be reduced.

One embodiment of a magnetic resonance imaging (MRI) scanner has a patient tunnel and a first receiving antenna for receiving a magnetic resonance signal from a patient. A patient is in the patient tunnel. The MRI scanner also has a second receiving antenna for receiving a signal having the Larmor frequency of the magnetic resonance signal, and a receiver. The receiver has a signal connection to the first receiving antenna and the second receiving antenna and may be configured to prepare the magnetic resonance signal for imaging.

The second receiving antenna is arranged outside or in the vicinity of an opening of the patient tunnel. An opening of the patient tunnel is seen, for example, as the openings through which the patient couch with the patient is moved into the patient tunnel and, depending on the region to be examined, also leave the patient tunnel again at the opposite end. In the vicinity may be, for example, a distance from the opening of less than 0.1 m, 0.2 m. 0.5 m, 1 m, or 2 m. In the vicinity may also be a distance from the opening of less than a quarter wavelength or a half wavelength of a radio wave in the air having a Larmor frequency of the MRI scanner.

The first receiving antenna may receive the magnetic resonance signal, which, however, always has a small portion of the interference signal. Conversely, the second receiving antenna not only receives the interference signal, but also a minimal or negligible portion of the magnetic resonance signal. For the sake of simplicity, the signal received by the first receiving antenna will still be referred to below as the magnetic resonance signal (e.g., even when having a portion of the interference signal to be removed), and the signal received by the second receiving antenna will be referred to as the interference signal.

The receiver is configured in this case to suppress an interference signal received with the second receiving antenna in a magnetic resonance signal received by the first receiving antenna.

The possibility is considered, for example, that the interference signal is more wideband than the magnetic resonance signal. The portions outside the frequency range of the magnetic resonance signal correlate in this case with the portions within the frequency range of the magnetic resonance signal. Therefore, it may also be sufficient in accordance with the present embodiments for the second receiving antenna to receive the wideband interference signal and for the receiver to be configured to evaluate this signal only partly (e.g., in a frequency range that is not the same as or is outside the frequency range of the magnetic resonance signal) and then to suppress the interference signal in a magnetic resonance signal received by the first receiving antenna as a function of this part signal. As an alternative or in addition, the second receiving antenna may already only receive frequencies outside the frequency range of the magnetic resonance signal and may forward these to the receiver. As a result of the correlation, for example, the amplitude of the frequency components of the interference signal in the frequency range of the magnetic resonance signal may be linked with an amplitude outside the frequency range. In this way, the second receiving antenna, in conjunction with the receiver during a magnetic resonance scan, may only monitor frequency components outside the frequency range of the magnetic resonance signal for interference signals and may suppress the interference signal in the signals of the first receiving antenna. In one embodiment, the receiver may establish a relationship between the interference signal from the first receiving antenna and the interference signal portion from the second receiving antenna (e.g., the transfer function) for an interference signal in the frequency range of the magnetic resonance signals between detections of magnetic resonance signals and during the detection of magnetic resonance signals, for example, to adapt the amplitude or scaling based on portions of the interference signal received by the second receiving antenna outside the frequency range of the magnetic resonance signal.

In one embodiment, a filter may be provided between the second receiving antenna and the receiver, which may let the interference signal through and suppresses magnetic resonance signals. For example, a filter that suppresses the magnetic resonance signals may be provided for an interference element with portions outside the frequency band of the magnetic resonance signal. The filter may also be adaptive or controllable. In this way, the interference suppression control may adapt the filter to the Larmor frequency of a slice currently being acquired.

An explanation is given below as to how the interference signal may be suppressed in the signals of second receiving antenna by the receiver. For example, the receiver may have a summation device, which forms a linear combination of one or more parameters dependent on the magnetic resonance signal and interference signal. Further, the receiver may have an interference suppression controller that is configured to vary the parameter or parameters such that an energy of the interference signal is minimal in the linear combination. In this case, one or more parameters may be complex in order to model a phase displacement, or a phase displacement may be specified by a separate parameter. A number of parameters, for example, allow the effective suppression of different interference sources.

Non-linear combinations of the signals depending on the parameter or parameters may also be provided, however.

The interference suppression controller may also weight interference signals with especially large amplitude especially heavily in the parameters compared to weaker interference signals in the interference suppression, since through the especially great distance of the signal level in relation to a statistical background interference, these strong interference signals are able to be suppressed especially well. In this case, different interference signals are, for example, seen as interference signals that may be separated by different point of origin using a number of second receiving antennas, occupy different frequency ranges, or are differentiated by different temporal behavior.

The receiver may be configured in this case to carry out this processing of the received magnetic resonance signal and of the interference signal for suppression of the interference signal in real time (e.g., by a field-programmable gate array (FPGA) or a digital signal processor (DSP)).

In one embodiment, the receiver may have a memory and may initially store the received interference signal and the received magnetic resonance signal, where the interference signal is only suppressed at a later point in time with a delay of, for example, the duration of an echo sequence, an excitation sequence, or an entire image acquisition of an individual slice or the entire image acquisition sequence. The delay may, for example, be greater than 50 ms, 100 ms, 0.5 s, 1 s, 10 s, 1 min, or more.

A receiver in the sense of the present embodiments may be seen as the hardware for analog and/or digital radio frequency processing such as, for example, amplifiers, filters, and mixers in real time, but also an image evaluation unit for later generation of an image from the received magnetic resonance signals.

The method of one or more of the present embodiments for operation of the MRI scanner of one or more of the present embodiments has the act of receiving interference signals by the receiver via the second receiving antenna. Because of the arrangement of the second antenna in the vicinity of the opening, the interference signal received by the second antenna received has scarcely any portions of the magnetic resonance signal or none at all.

In another act, the receiver receives a magnetic resonance signal via the first receiving antenna. The first receiving antenna may involve a body coil or a local coil of the MRI scanner, for example.

In a further act of the method, the receiver processes the magnetic resonance signal as a function of the interference signal by the receiver into a receive signal, where the dependency is a function of a parameter. For example, the receiver may form a linear combination of interference signal and magnetic resonance signal with the parameter as factor, where the parameter may be complex, in order to map a phase displacement. A number of parameters may also be provided.

In another form of embodiment of the method, the receiver may receive portions of a wideband interference signal outside the frequency range of the magnetic resonance signal using the second receiving antenna. In this case, portions of the interference signal outside the frequency range of the magnetic resonance signal correlate with portions within the frequency range. For example, the amplitudes of the interference signal within and outside the frequency range of the magnetic resonance signal may be proportional to one another if the same source is involved. In the suppression of the interference signal in the magnetic resonance signals received by the first receiving antenna described below, the scaling with the amplitude of the signal of the second receiving antenna may then be provided as the dependency, for example.

In an advantageous way, any influencing of the suppression of the interference signal by the magnetic resonance signals during an image acquisition may be avoided by the separate frequency ranges. In other words, by the evaluation of the signals received by the second receiving antenna by the receiver in frequency ranges that are not the same as the frequencies of the magnetic resonance signals, it may be avoided that scattered-in magnetic resonance signals are interpreted as an interference signal and suppressed by the interference suppression controller.

In one embodiment, in this case, the interference suppression controller also takes account of different characteristics of signals in the frequency band of the magnetic resonance signals and outside the frequency band. These may, for example, be different attenuations or signal delays, which may be taken into account by other amplification factors and phase displacements. The different characteristics may be established, for example, by calibration measurements to determine transfer functions, as will be explained below.

In this case, interference signals may be detected between and/or also during the MR signal acquisition by the receiver. A permanent detection allows the temporal course of an interference signal to be better detected and thus also better estimated for the future, which allows a more precise suppression.

An intermediate acquisition (e.g., between the acquisition of MR signals) makes it possible to avoid the MR signals being evaluated as interference signals. In this case, not only the second receiving antenna or antennas may detect the interference signals in this case, but also, simultaneously, the first receiving antenna or first receiving antennas may detect the interference signals, so that it is known exactly how an interference signal received by the second receiving antennas will be acquired by the first receiving antennas. This relationship, also referred to as a transfer function, then allows a more precise determination of parameters for interference suppression and thus a better suppression of the interference by the receiver.

The different methods (e.g., different frequency, temporal restriction) may also be combined with one another and/or employed alternately in order to arrive at an improved interference suppression overall.

In further embodiments, there may be an averaging of the results over longer or over a number of acquisition periods and/or also between the different methods.

In another act, the receiver, for example, by an interference suppression controller, sets the parameter such that a portion of the interference signal is reduced in the receive signal. In one embodiment, the parameter may be set by the interference suppression controller in an optimization method such that an energy of the interference signal is minimized in the receive signal.

As already explained previously for the receiver, the receiver in this case may also store the magnetic resonance signal and/or the interference signal in this case so that the acts of processing and of setting the parameters may also take place spaced apart in time from receipt of the signals by the first receiving antenna and the second receiving antenna.

In an embodiment, the MRI scanner of one or more of the present embodiments and the method for operation by the second receiving antenna and the receiver of one or more of the present embodiments make it possible to reduce the portion of external interference signals in the magnetic resonance signal and therefore to manage with simpler and lower-cost screening measures.

In a possible form of embodiment of the MRI scanner, the MRI scanner is configured to receive magnetic resonance signals having a Larmor frequency in an industrial band. A resonant frequency of the nuclear spins used for the imaging in the MRI scanner in a static magnetic field BO of a field magnet of the MRI scanner is referred to in this case as the Larmor frequency of the MRI scanner. Frequency bands released for use by medical or technical devices are referred to as, for example, the industrial band, for which simplified regulations for emission and approval are available. These are also referred to as Industrial, Scientific, Medical (ISM) bands. An example of a frequency band in which there may also be emissions with high powers, lies between 26.9 and 27.3 MHz. Other such frequency bands lie between 6.7 MHz and 6.8 MHz, 13.5 MHz and 13.6 MHz, 40.6 MHz and 40.7 MHz, and also 433.0 MHz and 434.8 MHz.

An MRI scanner is not only dependent on the lowest possible interference being received, but on the strong excitation pulses also not interfering with other devices. In the ISM band, the legal tolerance limits are significantly higher, so that a legally-conformant restriction through screening of the emitted excitation pulses is more easily possible at this frequency or even is not required. In synergistic connection with the active screening in order to suppress receive-side interference by other devices in the ISM band, an MRI scanner may be realized entirely without a screening cabin.

In a possible form of embodiment of the MRI scanner in this case, the MRI scanner has a transmit path for transmitting the excitation pulses with a filter. The filter in this case is configured to suppress signals outside the ISM band. For example, the filter may involve a bandpass filter for the ISM band used, that damps out frequencies outside the ISM band by more than 12 dB, 24 DB, 40 dB, or 60 dB relative to a signal with minimal attenuation within the ISM band. Depending on the implementation of the radio frequency generation of the MRI scanner, the filter may be arranged, for example, between final stage and a hybrid coupler, between hybrid coupler and transmit/receive switch, or between transmit/receive switch and transmit antenna.

The filter makes it possible to restrict radio frequency power transmitted essentially to the ISM band and in this way to adhere to the stricter limit values outside the ISM band. In this way, there may even be operation of the MRI scanner in the ISM band without an RF cabin.

In one embodiment, however, an ISM band with a screening cabin may be used without active interference suppression on the receive side (e.g., when the emissions by the excitation pulse are critical for an approval). This also applies to the forms of embodiment described below, which relate to a restriction or optimization of the excitation pulse for the ISM band.

In a form of an embodiment of the MRI scanner, the MRI scanner has a transmit antenna for transmitting an excitation pulse, where the MRI scanner has non-linear components for tuning the transmit antenna. These may be PIN diodes, for example, but also other diodes or active components such as transistors or FETs. In this case, the non-linear components are arranged in an area of the MRI scanner screened off from the patient tunnel for radio frequency, and the filter for the ISM band or ISM filter is arranged in the signal connection between non-linear component and antenna (e.g., in the screened-off area).

In one embodiment, by the screening-off of the non-linear components from the patient tunnel and the environment, emissions from frequency components that are created by the non-linearity during the excitation pulse by the components used for tuning, and as harmonics no longer lie in the ISM, are avoided. The filter prevents harmonics being transmitted via the signal connection between non-linear component and transmit antenna. In this way, the arrangement of the non-linear components contributes to adherence to emission limit values and makes it possible or simplifies dispensing with the screening of the entire MRI scanner by a radio frequency cabin.

In a possible form of embodiment of the MRI scanner of one or more of the present embodiments, the MRI scanner has a radio frequency unit with a preliminary interference suppressor. The preliminary interference suppressor is configured to provide preliminary interference suppression of the excitation pulse for excitation of the nuclear spins such that the signal components of the excitation pulse on transmission (e.g., after amplification by a radio frequency power amplifier outside the ISM band) are reduced by comparison with an excitation pulse without preliminary interference suppression. In one embodiment, for example, the preliminary interference suppressor may create and mix-in signal components that, after an amplification by the radio frequency unit, correspond to the harmonics created by the non-linearity of the radio frequency unit from the excitation pulse, but have a reversed leading sign; in this way, the harmonics reduce or extinguish each other. The preliminary interference suppressor in this case may be realized, for example, in a digital signal generator, or also, corresponding signals may be created from an input signal for a power amplifier by analog components. The preliminary interference suppressor in this case may also be adaptive (e.g., be controlled in its characteristics as a function of a loading of the patient tunnel). In one embodiment, a part regulation by a fast feedback from a sensor in the transmit path, such as, for example, a directional coupler, is provided.

In one embodiment, the preliminary interference suppressor reduces harmonics outside the ISM band and, in this way, facilitates or makes possible adherence to the emission limit values even without a screening cabin.

In a conceivable form of embodiment of the MRI scanner, a limit frequency for a propagation of a radio wave in the patient tunnel is greater than a Larmor frequency of the MRI scanner. The limit frequency is seen as the frequency at which a radio wave propagating in the longitudinal (e.g., z direction) through the patient tunnel may still form in the patient tunnel as a hollow conductor. The limit frequency is also referred to as the cut-off frequency for a waveguide (e.g., for the patient tunnel as a hollow conductor).

If the frequency of a radio signal lies below this, then there is an exponential drop in the field strength of an interference signal coming from outside with the distance from the opening inside the patient tunnel, so that the interference signal is significantly reduced in the examination region (e.g., Field of View (FoV)).

In a possible form of embodiment of the MRI scanner, the second receiving antenna is arranged at an opening of the patient tunnel or on the patient couch. For example, the second receiving antenna may be arranged directly at an edge of an opening or below the surface on which the patient lies.

For example, if the frequency of the interference signal lies below the limit frequency for a free wave, the patient and the patient tunnel form a coaxial conductor for the interference signal. A second receiving antenna in the vicinity of the patient and the opening may detect the interference signal coupled into the patient tunnel through the patient and, in this way, make possible an especially effective suppression by the receiver.

In a possible form of embodiment, the MRI scanner has a waveguide that surrounds the MRI scanner, where the waveguide has a limit frequency or cut-off frequency that is greater than the Larmor frequency of the MRI scanner. A waveguide in this case is seen as any electrically-conducting structure that surrounds the MRI scanner at least in four spatial directions around the outside (e.g., in the form of a tube or a prism) and through its conductivity at the Larmor frequency of the MRI scanner essentially suppresses a propagation of radio waves or electrical fields through the conducting structure. In other words, on a side of the electrically-conducting structure of the waveguide facing away from the MRI scanner, a signal with Larmor frequency is attenuated compared to a signal on the side facing towards the MRI scanner by more than 30 dB, 40 dB, 60 dB, or more.

In one embodiment, a waveguide of one or more of the present embodiments or even a classical screening cabin may surround the MRI scanner of one or more of the present embodiments. A radio-frequency-proof door to the screening cabin or the waveguide is replaced, however, in this case by an electrically conducting tunnel, which represents a waveguide with a cut-off frequency greater than the Larmor frequency.

Through the attenuation of the alternating fields in the tunnel, emission into the surroundings is reduced, so that an expensive RF-proof door that is difficult to use and susceptible to faults may be dispensed with (e.g., at the higher limit values for frequencies in ISM bands).

Use of a waveguide as door or screening is also basically conceivable without any active interference suppression in the receive path.

In a conceivable form of embodiment of the MRI scanner, the waveguide has an electrically conductive connection to the patient tunnel. In this case, the waveguide together with the patient tunnel may embody an end-to-end or contiguous waveguide. In one embodiment, the waveguide may be connected electrically at both ends of the patient tunnel to the patient tunnel, or two waveguides at opposite ends of the patient tunnel may be connected electrically-conductively to the tunnel. In this case, the waveguide may also have a limit frequency or cut-off frequency that is different from the limit frequency of the patient tunnel but is likewise above the Larmor frequency of the MRI scanner.

In a conceivable form of embodiment of the MRI scanner, the second receiving antenna has an essentially omnidirectional receive characteristic. An essentially omnidirectional receive characteristic is seen as a sensitivity distribution of the receiving antenna in all spatial directions, in which the difference between a maximum sensitivity and a minimum sensitivity as a function of the different directions is less than 6 dB, 12 dB, 18 dB, or 24 dB. This may also apply to different polarizations of the interference signal.

The incident interference signal may come from different directions and with different polarizations, so that an antenna with a directional characteristic or preferred polarization cannot detect all interference signals. An antenna with an omnidirectional receive characteristic, however, may detect all interference signals.

In a possible form of embodiment of the MRI scanner, the MRI scanner has a plurality of second antennas and the receiver is configured to suppress the interference signal in the magnetic resonance signal as a function of receive signals of the plurality of second receiving antennas. In one embodiment, the plurality of second receiving antennas are arranged spaced apart from one another (e.g., at a distance greater than a quarter of a wavelength or a half wavelength of a radio wave having the Larmor frequency).

In one embodiment, a plurality of spatially distributed antennas is also better suited to detecting one or more interference sources and thus to improving the interference suppression.

In a conceivable form of embodiment of the MRI scanner, the plurality of receiving antennas is arranged in a symmetry arrangement in relation to the patient tunnel. In one embodiment, an arrangement at the edge of the opening of the patient tunnel at two opposite points, on the corner points of a regular polygon or polyeder, is provided.

A symmetry relationship of the parameters may also be produced by the symmetry of the antennas; in this way, the optimization method for reducing the interference signal may be simplified and/or speeded up.

In a possible form of embodiment of the MRI scanner, the MRI scanner has an interference suppression transmitter and an interference suppression antenna. The interference suppression antenna is arranged at a distance from the patient tunnel. The interference suppression transmitter is configured in this case to generate a signal in a frequency range of an excitation pulse of the MRI scanner and to output the signal via the interference suppression antenna such that a field strength of the excitation pulse will be reduced by destructive interference in an area surrounding the MRI scanner. Reduced is seen as reduction of the field strength or attenuation of the signal of the excitation pulse in the area by more than 6 dB, 12 dB, 24 dB, 40 dB, or 60 dB.

In one embodiment, the field strength of the electromagnetic waves emitted by the excitation pulse in the environment of the MRI scanner may be reduced by the interference suppression transmitter and the interference suppression antenna (e.g., in synergy with the other proposed measures), such that even without an RF cabin, the legal limit values may be adhered to.

In a conceivable form of embodiment of the MRI scanner, the MRI scanner has a plurality of interference suppression antennas, where the interference suppression antennas are arranged at a distance from the patient tunnel and relative to one another. The distances may be less than a wavelength of a free radio wave having the Larmor frequency and/or greater than a tenth of the wavelength. For example, the interference suppression antennas may be arranged in a plane around the opening of the patient tunnel. The interference suppression transmitter is configured to output signals in a frequency range of an excitation pulse of the MRI scanner via the interference suppression antennas, so that a field strength of the excitation pulse is reduced by destructive interference in a number of areas of an environment of the MRI scanner.

In one embodiment, it is possible with a number of interference suppression antennas and activation signals of the interference suppression transmitter to reduce the electromagnetic fields in a number of areas or to reduce the emissions in a number of directions or to bring the emissions down to zero. The number of directions without emissions in this case corresponds to zero points of the emission diagram of a multipole. A resulting electromagnetic wave from a signal of the excitation pulse from a local transmit antenna and the interference suppression antennas is thus as a multipole field (e.g., quadrupole field) that drops significantly more quickly as the distance from the source increases than a dipole field, for example, and in this way, makes it possible to adhere to limit values for emissions even without an RF cabin.

In a possible form of embodiment of the MRI scanner, the interference suppression transmitter is configured to generate the signals for the interference suppression antenna or interference suppression antennas by phase displacement and/or amplitude adaptation as a function of one or more transmission interference suppression parameters. In one embodiment, the respective signal or signals for the interference suppression antenna or interference suppression antennas are generated from the excitation pulse by adjustable amplifiers or attenuators and phase displacement elements in the interference suppression transmitter. The amplitude relationships and phase displacements in this case may represent the transmit interference suppression parameters or may be derived from the transmit interference suppression parameter or transmit interference suppression parameters (e.g., by analytical functions, tables, or iteration methods).

The excitation pulse in this case may be detected, for example, via a sensor such as a directional coupler in the line between radio frequency power amplifier and transmit antenna or a sensor antenna in the patient tunnel. In one embodiment, the signals for the interference suppression antennas may be generated directly from the digital data of the excitation pulse by scaling and phase displacement with A/D converters and amplifiers.

In one embodiment, transmit interference suppression parameters, by reducing the number of variables, simplify a subsequently specified determination of the setting of the interference suppression transmitter and make possible a more rapid adaptation to changed conditions such as other excitation pulses or being surrounded by patient or operating personnel.

In a possible form of embodiment of the MRI scanner, the transmit interference suppression parameters are set when the installation is manufactured.

In a conceivable form of embodiment of the MRI scanner, the MRI scanner has a calibration element in an environment of the MRI scanner and an interference suppression controller. The calibration element may be an antenna or sensor with which an electrical and/or magnetic field strength of an electrical and/or magnetic alternating field with a frequency of the excitation pulse is detected and may be forwarded to the interference suppression controller. The interference suppression controller is configured to detect a field strength in a frequency range of an excitation pulse at the location of the calibration element using the calibration element. For example, the interference suppression controller may have a calibration receiver. The interference suppression controller is further configured, depending on the detected field strength, to set the transmit interference suppression parameters such that a field strength of the excitation pulse is reduced in a predetermined environment of the calibration element. For example, the interference suppression controller may vary or optimize an amplitude and/or phase of the interference suppression antenna or antennas such that a reduction and/or a local minimum of the field strength is obtained by destructive interference at the location of the calibration element.

In one embodiment, by the adaptive setting of the transmit interference suppression parameter or parameters, there may be a reaction to an environment changed by persons or equipment in the environment of the MRI scanner, in order to adhere to the limit values for emission even under changing conditions. If necessary, the transmission may be interrupted and/or a new determination of the parameters may be initiated if a limit value is exceeded.

In a possible form of embodiment of the MRI scanner, the interference suppression antenna has a radio frequency power amplifier. The radio frequency power amplifier may be configured, in this case, to generate an electromagnetic alternating field sufficient for suppression of stray fields of the excitation pulse via the interference suppression antenna from an activation signal with a low radio frequency power (e.g., less than 10 mW, 50 mW, or 100 mW).

The radio frequency power amplifier makes it possible, compared to a purely passive interference suppression antenna, to connect this by a thin, flexible radio frequency cable to the interference suppression transmitter and, in this way, to simplify the installation. In interaction with the patient tunnel as waveguide and the plurality of interference suppression antennas, in this case, only a power in the range of a few watts is required, so that the locally arranged radio frequency power amplifier may be made small and light, which simplifies the installation.

In this case, the transmission interference suppression of one or more of the present embodiments by destructive interference may also be applied independently of the other features of the MRI scanner of one or more of the present embodiments. For example, use of an active interference suppression transmitter even without active receive-side interference suppression may be provided (e.g., when the permitted electromagnetic radiation is the limiting factor).

Particular synergies are produced, however, in ISM bands by the higher permitted limit values, which in conjunction with a receive-side interference suppression, make operation possible even without closed screening cabins.

In a conceivable form of embodiment of the method, the act of setting the parameter has the act of an averaging over time with the formation of a temporal average value as a function of the interference signal. For example, the amplitude and/or phase of the interference signal may be detected and averaged via a lowpass or by forming the average over a window, so that the parameter only follows slow changes.

In one embodiment, the averaging over time leads to the interference suppression not being falsified by short-term, possibly sporadic influences, and to higher-frequency interference components not being artificially created by the interference suppression.

In a possible form of embodiment of the method with an MRI scanner with calibration element, the setting act includes the following sub-acts.

In one act, the receiver measures a first transfer function between a first receiving antenna and the calibration element. The measurement may take place, for example, by the receiver or the interference suppression controller instructing the interference suppression transmitter via a signal connection to transmit a signal with a predetermined amplitude and/or predetermined phase in a frequency range of the magnetic resonance signal and/or in an adjacent frequency range via the calibration antenna. In this case, a signal connection between interference suppression transmitter and calibration element is necessary. The receiver may then receive the signal via the first receiving antenna and define a first transfer function in this way. This may also occur simultaneously for a number of first receiving antennas. The transfer function may, however, also be detected by transmitting via the first receiving antenna and receiving via the calibration element.

In a further act, the receiver measures a second transfer function between the second receiving antenna and the calibration element. This may take place in the same way as previously described. If the signal is transmitted via the calibration element, then both transfer functions may be detected at the same time.

In one embodiment, the signals transmitted for detection of the first transfer function and the second transfer functions are encoded so that the receiver may establish the amplitude and phase relationship in a simple way. For example, a pseudo random code that allows a fast and safe autocorrelation of the signals may be provided. The signal in this case may be modulated in amplitude, frequency, and/or phase. In one embodiment, spread-spectrum modulations, in which the signal for establishing the transfer function may also remain below the noise limit of the MR signals and a simultaneous transmission is possible during a detection of an MR signal, may be provided. In this way, changes in the environment may be addressed permanently. The permanent emission of the signal may also be achieved by use of a frequency range adjacent to the MR signals. Then, however, the different propagation conditions by the different frequencies in the determination of the transfer functions are to be taken into account.

In a further act, the interference suppression parameter, or with a number of first and second receiving antennas, the interference suppression parameters are set as a function of the measured first transfer function or transfer functions and second transfer function or transfer functions, so that a portion of an interference signal received by the second receiving antenna or antennas is reduced in a signal received by the receiver via the first receiving antenna. In this case, the interference signal received by the second receiving antenna or antenna may also continue to be taken into account. The transfer functions in this case are applied to the form in which the signal of an individual receiving antenna is taken into account. This may be achieved, for example, by the interference suppression parameters for the interference signal separated via an autocorrelation in the received MR signal being set by a variation method or linear optimization method by the interference suppression controller, such that the interference signal portion is minimized. In this case, the transfer functions are included as predetermined attenuations and phase displacements between receiving antennas and receiver. For a calibration element, the transfer function in this case in precise terms is only valid for an interference source at a specific location or direction. When sufficiently many and suitably positioned calibration elements are used to determine the transfer functions, transfer functions may also be determined independently of the respective location of the calibration element.

In one embodiment, the determination of the transfer functions using the calibration element makes it possible for the receive interference suppression to react to different conditions in the environment, such as, for example, position of people or equipment and the propagation conditions changed thereby, and to adapt the interference suppression.

In a possible form of embodiment of the method, the setting act occurs in a period of a sequence in which no magnetic resonance signal is received (e.g., also no signal for excitation of the spins is sent). Within a sequence for image acquisition, there are periods of time in which no excitation pulses are emitted and also there is no acquisition of a magnetic resonance signal for imaging. In one embodiment, this involves periods of the sequence in which the examination object or the patient is not emitting any appreciable magnetic resonance signal (e.g., the level of the signal is at least 12 dB, 24 dB, 36 dB 48 dB, or 60 dB below a maximum magnetic resonance signal). In this form of embodiment of the method, the setting act takes place in such a period.

The interference suppression controller of the receiver is correspondingly configured to carry out the setting act in such a period. For example, the interference suppression controller may receive a trigger signal from the controller of the MRI scanner.

In one embodiment, the setting of the parameters may be simplified without a magnetic resonance signal (e.g., by an energy of the signal received by the first receiving antenna being minimized as a function of the parameters). Even if the interference signal changes in amplitude over time, for example, the parameters set continue to remain valid and effective with the same spatial arrangement.

In another possible form of embodiment of the method, the setting of the parameter may take place permanently (e.g., in short intervals of 1 ms, 10 ms, or 100 ms or in real time with a delay of less than 10, 100, or 500 microseconds).

In one embodiment, the permanent setting of the parameter in real time or almost in real time allows there to be a reaction to new interference signals occurring and a negative effect of the new interference signals on the imaging to be minimized as much as possible.

In a further form of embodiment, the receiver has a memory and stores the received magnetic resonance signal and the received interference signal. The receiver in this case may, for example, also include an image evaluation processor. In one embodiment, however, the receiver in the narrower sense (e.g., the devices used for editing the received radio frequency magnetic resonance signals) may include the memory. The setting of the parameters and the processing of the magnetic resonance signal with the interference signal as a function of the parameter for reduction of the interference signal by the receiver to a receive signal may then take place with a delay to the receipt. The delay may, for example, include the duration of an echo sequence or also of an entire image acquisition sequence (e.g., more than 10 ms, 100 ms, 0.5 s, 10 s, or even several minutes, hours, or days).

In one embodiment, the storage makes it possible to use resources of the MRI scanner already available as well or, on account of the fact that real time processing is not required, also to provide the interference suppression at lower cost with less computing power. The retroactive interference suppression also makes possible a comparison of results of different parameter settings and suppression methods and thus an optimization of the interference suppression.

In one conceivable form of embodiment of the method, the receiver or the interference suppression controller has an autocorrelation facility. The interference suppression controller may determine a portion of the interference signal in the magnetic resonance signal (e.g., an amplitude and a phase displacement) using the autocorrelation facility.

In another possible form of embodiment, the interference suppression controller has an estimation device that, for example, establishes the portion of the interference signal by an optimization method in which the interference portion is minimized in the magnetic resonance signal by variation of the parameter or the parameters, such as by Least Mean Square Root (LSR) or similar methods.

With a number of parameters, the interference suppression controller optimizes the plurality of the parameters such that as large a portion of the interference signal as possible is reduced. This may be of advantage, for example, with a number of interference sources or reflections.

In one embodiment, autocorrelation or estimation allow a flexible adaptation to different interference sources.

In a possible form of embodiment of the method, the act of setting the parameters has the following sub-acts.

In one sub-act, the received magnetic resonance signals are transformed into an image space. In this case, the usual methods used in MR imaging such as, for example, a Fourier transform are used, but also, other methods such as compressed sensing may be used.

In another sub-act of the method, the interference signals are separated in the image space from the magnetic resonance data. This may take place, for example, by comparing two adjacent volumes or by two items of image data of the same volume acquired at different points in time. While the image data is the same or similar, image artifacts created by interference signals are markedly different on account of the lack of correlation.

In one embodiment, the acquired image space or the associated volume may be greater than the examination object. Regions that do not have any magnetic resonance signal, but merely interference signals, are then detected in the image space. Through this segmentation, the interference signal may be separated and established.

In a further sub-act, the interference signals separated in the image space are transformed back into a raw data space or k-space (e.g., once more with a Fourier transform).

In another sub-act, the parameters for the suppression of the interference signals are determined from the transformed interference signals in the raw data space. For example, the coordinates in the k-space specify information about phase and frequency of an interference signal, so that taking into account the arrangement of the first receiving antenna and second receiving antenna and also attenuation factors and phase displacement of the signal paths, an attenuation and signal delay may be determined, after the application of which to the interference signal of the second receiving antenna in a sum signal with the receive signal of the first receiving antenna, the interference in the magnetic resonance signal is reduced.

In one embodiment, however, the interference signals may be suppressed directly in the image space (e.g., by hiding the corresponding image data). This may be used, for example, when the image data does not lie in the examination region or may be replaced by data without any interference already acquired from this region. In one embodiment, the data with interference may be identified in the image space by a particular indicator (e.g., a color or brightness value), so that image artifacts caused by interference may not be taken for features of the examination object.

In one embodiment, the recognition of the interference signals in the image space allows a separation or segmentation of magnetic resonance data and interference. This enables the interference signals to be acquired separately in a simple way and the characteristics to be better identified, which leads to a better and more effective suppression.

In a conceivable form of embodiment of the method, the sub-acts of the transformation, of the separation, of the back transformation, and of the determination of the parameters on rows of data in the received magnetic resonance signals take place in the raw data space.

Through the application of the method of one or more of the present embodiments to individual rows of the raw data space and corresponding transforms in the image space, the parameters may be changed more quickly than, for example, during acquisition of an entire slice, and there may thus be a faster reaction to changes of the interference signals. A repetition of the acquisition for an entire slice may be avoided in this way.

In a possible form of embodiment of the method, the receiver monitors the interference signal in one act for changes and adapts the parameters in a further act if there is a change. For example, it is possible, through a movement of the interference source or a reflecting object in the environment of the MRI scanner, for the field distribution of the interference source to change in phase and amplitude. The receiver may then detect such changes of the interference signal and adapt the parameter or the parameters accordingly, so that, for example, the interference signal received by the second receiving antenna or the second receiving antennas is added to the MRI signal with adapted amplification and/or phase displacement. In this case, the receiver may take account of threshold values during the monitoring, and only a threshold value being exceeded may be seen as a change. In one embodiment, the receiver may undertake an averaging over time in order to edit out short-term fluctuations. The averaging in this case may, for example, involve characteristics of the interference signal such as amplitude, phase, frequency, and/or frequency distribution in order not to react to short-term fluctuations and to introduce as few additional noise components into the magnetic resonance signal by the interference suppression as possible. In one embodiment, the parameters may be averaged over a period of time or may be filtered with a lowpass during the setting act.

In one embodiment, a monitoring of the interference signal by the receiver allows there to be a reaction to changes of the interference signal and thus provide effective noise suppression over a longer period of time of a variable interference signal. Thresholds and averaging in this case allow the changes to be limited and variations caused by instabilities or artifacts caused by compensation that is too great to be avoided.

In a possible form of embodiment of the method, the receiver stores a first received magnetic resonance signal in a memory in one sub-act. In another sub-act, the receiver stores a second received magnetic resonance signal in a memory. In a further sub-act, the receiver compares the first received magnetic resonance signal and the second received magnetic resonance signal. If the receiver recognizes a deviation in this process that is to be attributed to external interference sources, the receiver carries out an interference suppression measure or signals a fault to the controller of the MRI scanner, so that this initiates the interference suppression measure. Sudden differences in amplitude in magnetic resonance signals of slices lying close to one another or measurements of the same slice (e.g., from a calibration measurement) may thus possibly be interference signals.

In one embodiment, interference signals may be recognized by the comparison of the magnetic resonance signals of adjacent regions or the same regions at different times. This is also conceivable in an application without second receiving antenna for receiving the interference signal.

In a conceivable form of embodiment of the method, the interference suppression measure is the discarding of the first received magnetic resonance signal and/or the second received magnetic resonance signal. In one embodiment, in addition or as an alternative, an acquisition of the first magnetic resonance signal and/or the second magnetic resonance signal may be repeated. The interference suppression measure may also include a setting of the parameter.

Through the interference suppression measures of the present embodiments, image artifacts in the magnetic resonance recordings after recognition of an interference signal may be avoided.

In a possible form of embodiment of the method for operation of an MRI scanner, the MRI scanner has a patient tunnel, a first receiving antenna for receiving a magnetic resonance signal from a patient in the patient tunnel, a second receiving antenna for receiving a signal with the Larmor frequency of the magnetic resonance signal, and a receiver. The second receiving antenna is arranged outside the patient tunnel or in the vicinity of an opening of the patient tunnel. The method has the act of receipt of an interference signal by the receiver via the second receiving antenna. Through the arrangement of the second receiving antenna, the antenna is more sensitive to signals outside the patient tunnel, which, merely because of spatial origin, cannot be magnetic resonance signals. The signal of the second receiving antenna may also have small portions of a magnetic resonance signal, but because of the small portion, may not be considered initially for the interference suppression or may be further reduced or avoided with device and methods specified herein.

In another act, the receiver receives a magnetic resonance signal via the first receiving antenna. In this case, the signal that is primarily used for image acquisition is referred to as the magnetic resonance signal. For example, the first receiving antennas may involve local coils on the body of the patient. The magnetic resonance signal may contain portions of the interference signal, which are to be further reduced with the facility or method of the present embodiments, as described below.

In a further act, the received magnetic resonance signal of the first receiving antenna is discarded depending on the interference signal received by the second antenna. For example, the interference signal received by the second receiving antenna may lie above a threshold level, so that despite the propagation attenuation between location of the second receiving antenna and location of the first receiving antenna, a fault is to be expected from the image obtained from the magnetic resonance signal. The receiver or the control of the MRI scanner may then discard the signal of the first receiving antenna. In one embodiment, the MRI scanner may then subsequently repeat the acquisition of the discarded signal.

In one embodiment, an interference signal may already be recognized based on the signal amplitudes by the different arrangement of the first receiving antenna and the second receiving antenna.

In a conceivable form of embodiment of the method for operation of an MRI scanner having a Larmor frequency in an ISM band, the method has the act of determining an excitation pulse for excitation of nuclear spins in an examination object. The determination in this case takes place as a function of predetermined frequency limits of the ISM band. In one embodiment, the excitation pulse is determined such that the excitation pulse only has spectral portions outside the ISM band below predetermined threshold values. The restriction to the ISM band may be achieved, for example, by the measures described below.

In another act of the method, the MRI scanner emits the excitation pulse. In a further act of the method, the MRI scanner receives a magnetic resonance signal, and in another act, establishes a mapping of a distribution of nuclear spins in the examination object. The mapping may subsequently be output on a display.

Within the ISM band, markedly higher limit values for radio waves emitted into the environment are usually allowed. Excitation pulses, depending on slice density and duration, may be so wideband that the excitation pulses have portions outside the ISM band, even if the Larmor frequency lies within the ISM band. If this is avoided by the measures explained below, then additional measures such as an RF cabin may be dispensed with without exceeding the limit values.

In a possible form of embodiment of the method, the act of determining an excitation pulse has the sub-acts of determining an excitation pulse to excite the nuclear spins in a slice of the examination object as a function of a relative position of the slice for a magnet unit, of a predetermined gradient strength, of a thickness of a slice, and of the type of measurement. This may take place, for example, by using parameterized libraries on excitation pulses.

In a further test act, it is established by the MRI scanner whether the excitation pulse lies within the predetermined frequency limits. This may take place, for example, by spectral analysis using FFT.

If the excitation pulse does not lie within the predetermined frequency limits, the establishing acts are repeated. In these, a pulse parameter is varied, which, on establishing the excitation pulse, has an effect on a spectral frequency distribution of the excitation pulse.

If the excitation pulse lies within the predetermined frequency limits, the excitation pulse is emitted in a further act by the MRI scanner.

In a conceivable form of embodiment of the method, the pulse parameter with an effect on the establishing of the excitation pulse is: duration of the excitation pulse; thickness of the slice; or relative position of the slice or strength of the gradients. In other words, to obtain a different excitation pulse that lies within the ISM frequency band having the Larmor frequency of the MRI scanner, the duration of the excitation pulse, the thickness of the slice to be excited, or also the position of the slice or the strength of the gradients may be changed, for example. A simultaneous variation of a number of parameters may also be provided.

By variation of one or more pulse parameters, an excitation pulse may be established in an advantageous way that does not exceed the limits of the frequency band and in this way makes operation within the permitted framework possible.

In a possible form of embodiment of the method, the act of emission has the sub-act of altering the position of the examination object relative to the magnet unit before the act of emitting the pulse.

Through the gradient fields, it may occur at the edges of the FoV that the resonant frequency of the nuclear spins deviates more strongly from the average Larmor frequency of the MRI scanner established by the BO field. By repositioning the slice to be acquired more towards the isocenter of the BO field, with the same bandwidth of the excitation pulse, a complete excitation of a slice may be obtained, without departing from the band limits of the ISM band.

In a possible form of embodiment of the MRI scanner, the MRI scanner has a control unit for controlling the image acquisition, which, for example, may influence parameters of the image acquisition such as time of the excitation pulse and/or time of the acquisition of the magnetic resonance signal, or also frequency of the excitation pulse and/or frequency range of the receiver on receipt of the magnetic resonance signal. Further, the MRI scanner has an interface connected to the control unit for signaling. The interface, as explained below, may be an interface for exchange of data with other magnetic resonance systems or also a radio frequency interface. The control unit is configured to synchronize an image acquisition as a function of a signal received by another MRI scanner via the interface. Synchronization is, for example, seen as any activity that reduces mutual interference. This may include time coordination, but also, for example, a change of frequencies.

In an embodiment of the MRI scanner, the control unit may also be configured to transmit a signal with information about an impending image acquisition to another MRI scanner. This feature, in a similar way to a plug and socket connection, supplements the aforementioned MRI scanner, which is configured to receive a signal from another MRI scanner. The information may relate to a time of emission and/or frequency of an excitation pulse. In one embodiment, the MRI scanner, as explained below, is configured both for transmitting and also for receiving a signal. The MRI scanner will also be referred to below as the first MRI scanner.

A signaling connection may also be established between the first MRI scanner of one or more of the present embodiments and a second MRI scanner. The first MRI scanner and the second MRI scanner each have an interface and a control unit for this purpose. The first MRI scanner and the second MRI scanner are connected for signaling via the interfaces. The signal connection makes it possible at least to transmit a signal from the first MRI scanner to the second MRI scanner, but a bidirectional exchange of information may also be provided. Point-to-point connections on an electrical, optical, or wireless path may be provided. Networks such as LAN, WAN, specifically TCP/IP, are also possible as a signal connection. The control unit of the first MRI scanner is configured to transmit information for an impending image acquisition process via the interface to the second MRI scanner. A time of a planned emission of an excitation pulse in absolute time or relative to the signal, or also to the frequency of a frequency range of the excitation pulse may be provided. The control unit of the second MRI scanner is configured in this case to receive the information via the interface and to carry out an image acquisition as a function of the received information. For example, the control of the second MRI scanner may be configured to shift the acquisition of a magnetic resonance signal (e.g., a sequence or a part thereof) in time so that the magnetic resonance signal does not disturb the excitation pulse of the first MRI scanner. The second MRI scanner is also referred to below as the other MRI scanner.

The method of one or more of the present embodiments for operation of an MRI scanner may also be expanded for operation of a first MRI scanner with a control unit for controlling the image acquisition and an interface connected to the control unit for signaling. The method then has the act of receipt of a signal by the control unit via the interface from a second MRI scanner. This may involve an explicit exchange of information, in which the first MRI scanner receives information or a message from the second MRI scanner via a data interface, which features parameters such as time and/or frequency of an intended image acquisition. In one embodiment, the first MRI scanner may monitor the environment, for example, via a receiver for magnetic resonance signals.

In another act, the control unit of the first MRI scanner sets a parameter of the image acquisition as a function of the received signal. In one embodiment, a sequence may be shifted in time.

In a further act, an image acquisition according to the parameter set is carried out by the first MRI scanner. For example, the sequence may be begun at a changed point in time, so that the excitation pulses of both MRI scanners occur at the same time or the excitation pulse of the first MRI scanner occurs at a point in time at which the second MRI scanner is not receiving any image-relevant magnetic resonance signals.

In one embodiment, the MRI scanner of one or more of the present embodiments, in conjunction with a second MRI scanner and the method for operation, enable mutual interference by two MRI scanners during simultaneous operation to be reduced.

In a possible form of embodiment of the MRI scanner, the interface is configured for the exchange of data. In other words, the first MRI scanner is configured both to transmit data via the interface to a second MRI scanner and also to receive data via the interface data from a second MRI scanner. In this case, the control unit is configured, by exchange of information via the interface, to synchronize an image acquisition with a second MRI scanner. In other words, the control units agree between themselves, by messages, how the image acquisition takes place, so that mutual disruptions are reduced.

In a conceivable form of embodiment of the MRI scanner, the signal has information about a time and/or frequency of a transmit process. The time in this case may be specified in absolute terms, for example, or relative to the time at which the message was sent. A mid frequency and/or a bandwidth, a frequency range, or also a channel specification that encodes a frequency range may be given as a specification.

In a possible form of embodiment of the method for operation of a first MRI scanner and a second MRI scanner, the method also has the act of establishing information about an impending image acquisition of the second MRI scanner by a control unit of the second MRI scanner and, in a further act, of transmitting a signal with the information to the first MRI scanner.

For example, the control unit may receive, via the interface, a message from a second MRI scanner that the scanner will transmit an excitation pulse with a mid frequency equal to the Larmor frequency+100 kHz with a bandwidth of 200 kHz in 2 seconds. The first MRI scanner may then, for example, interrupt a sequence before its own excitation pulse and continue after the second MRI scanner has ended its sequence, or transmit the next excitation pulse simultaneously with the excitation pulse of the second MRI scanner. Mutual disruption by an excitation pulse of the second MRI scanner during a receive phase may be avoided in this way.

In a possible form of embodiment of the MRI scanner, the signal has information about a time and/or frequency of a receive process. The information may specify a beginning or a duration and frequency, for example, as to how there will be receiving from the second MRI scanner beginning in a second for 2 seconds at a mid frequency equal to the Larmor frequency minus 300 kHz with a bandwidth of 200 kHz. The first MRI scanner may then, for example, interrupt a sequence such that the sequence does not transmit an excitation pulse in this time in the frequency band.

In one embodiment, even on receipt of a message about a planned receipt in other units, an emission of the first MRI scanner may be shifted so that a disruption is reduced.

In a possible form of embodiment, the control unit of the first MRI scanner may be configured to change the frequency of an image acquisition process as a function of the received information. For example, an image acquisition may include different slices, where these are differentiated by a gradient magnetic field in the z-axis and thus in the effective Larmor frequency of the magnetic resonance signal. In this way, a simultaneous operation with reduced interaction is possible, provided the order of the slices in the image acquisition is arranged so that there is never an acquisition in the same frequency range in both systems.

In one embodiment, the differentiation via the frequency makes possible a simultaneous acquisition of the magnetic resonance signals in adjacent MRI scanners and thus a better use of the examination time.

In a conceivable form of embodiment of the MRI scanner, the first MRI scanner has a receiver as the interface. A receiver is seen, for example, as a receiver for magnetic resonance signals including an antenna such as a local coil or body coil. In this case, the first MRI scanner is configured to acquire an excitation pulse of a second MRI scanner outside an image acquisition and to carry out the image acquisition as a function of the acquired excitation pulse. For example, the first MRI scanner may then initially acquire or wait for magnetic resonance signals of a slice with another effective Larmor frequency, until a maximum duration for an acquisition of magnetic resonance signals has elapsed in the second MRI scanner emitting the excitation pulse.

In this way, the synchronization may be undertaken even without a data connection or changes in the second MRI scanner.

In a possible form of embodiment of the method for operation of a first MRI scanner and a second MRI scanner, the method also includes the act of establishing information about an impending image acquisition of the second MRI scanner by a control unit of the second MRI scanner and in a further act, of transmitting a signal with the information to the first MRI scanner.

In one embodiment, the different measures described may be combined with one another. A protocol for an exchange of information in two MRI scanners may also be provided, through which the image acquisitions from both systems are interleaved with one another in an optimized way, so that the duration of the acquisition only changes slightly without any mutual disruptions occurring. In the simplest case, all excitation pulses may be undertaken at the same time, for example, provided an image acquisition is taking place in both MRI scanners in the same period of time.

DETAILED DESCRIPTION OF THE DRAWINGS

Figure 1:
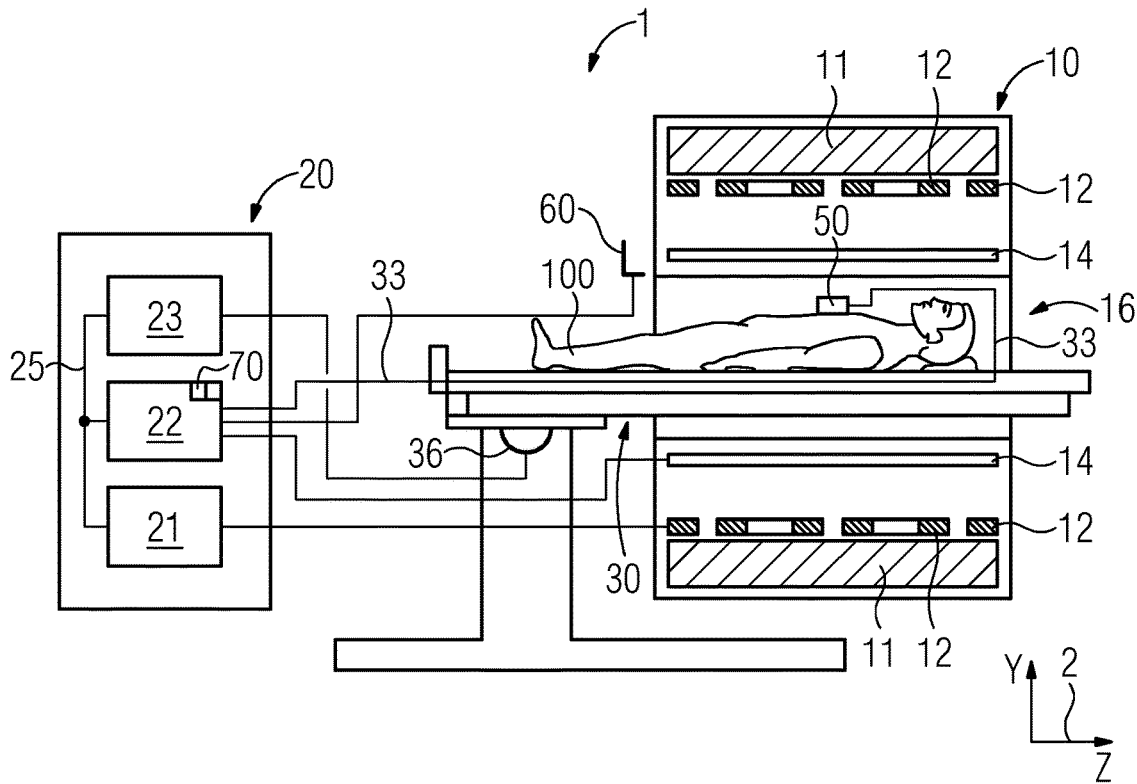
FIG. 1 shows a schematic diagram of a magnetic resonance imaging (MRI) scanner with an embodiment of a facility.

FIG. 1 shows a schematic diagram of a form of embodiment of a magnetic resonance imaging (MRI) scanner 1 with one embodiment of a local coil 50.

A magnet unit 10 has a field magnet 11 that creates a static magnetic field BO for alignment of nuclear spins of samples or of a patient 100 in a recording region. The recording region is characterized by an extremely homogeneous static magnetic field BO, where the homogeneity relates, for example, to a magnetic field strength or an amount. The recording region is almost spherical and is arranged in a patient tunnel 16 that extends in a longitudinal direction 2 through the magnet unit 10. A patient couch 30 is able to be moved in a patient tunnel 16 by a drive unit 36. the field magnet 11 may involve a superconducting magnet that may provide magnetic fields with a magnetic flux density of up to 3T or more. For lower field strengths, however, permanent magnets or electromagnets with normally conducting coils may be used.

The magnet unit 10 has gradient coils 12 configured for spatial differentiation of the acquired imaging regions in the examination volume by superimposing variable magnetic fields on the magnetic field BO in three spatial directions. The gradient coils 12 may be coils made of normally conductive wires that may create fields orthogonal to one another in the examination volume.

The magnet unit 10 likewise has a body coil 14 configured to irradiate a radio frequency signal supplied via a signal line into the examination volume and to receive resonant signals emitted from the patient 100 and output the resonant signals via a signal line.

A control unit 20 (e.g., a controller) supplies the magnet unit 10 with the various signals for the gradient coils 12 and the body coil 14 and evaluates the received signals.

In this way, the control unit 20 has a gradient controller 21 configured to supply the gradient coils 12 with variable currents via supply lines that, when timing is coordinated, provide the desired gradient fields in the examination volume.

The control unit 20 has a radio frequency unit 22 configured to generate a radio frequency pulse with a predetermined temporal course, amplitude, and spectral power distribution to excite a magnetic resonance of the nuclear spins in the patient 100. In this case, pulse powers in the kilowatt range may be achieved. The excitation pulses may be irradiated into the patient 100 via the body coil 14 or also via a local transmit antenna.

A controller 23 communicates via a signal bus 25 with the gradient control 21 and the radio frequency unit 22.

A local coil 50 is arranged on the patient 100 as a first receive coil, which is connected to the radio frequency unit 22 and a corresponding receiver via a connecting line 33. In one embodiment, the body coil 14 may be a first receiving antenna in the sense of the present embodiments.

Arranged at an edge of the opening of the patient tunnel 16 are four second receiving antennas 60 that are arranged at the corners of a square, which is encompassed by the circular opening, so that the corners lie on the edge of the opening. The four second receiving antennas 60 are connected to the receiver 70 of the radio frequency unit 22 for signaling. As a result of the plurality of second receiving antennas 60, the plurality of second receiving antennas 60 may not all have an omnidirectional receive characteristic, but may be dipoles, for example, and may supplement each other to form an omnidirectional receive characteristic by different alignment of the plurality of second receiving antennas 60. In one embodiment, a crossed-dipole as a single second antenna with omnidirectional receive characteristic is provided.

In one embodiment, as an alternative or in addition, a second receiving antenna 60 may be arranged in the patient couch 30.

The patient tunnel in this case may have a radius R for which the following applies:

$$R < (\text{Lambda}_L * 1.841)/(2 * \text{Pi})$$

Lambda$_L$ in this case specifies the wavelength of a radio wave in air at the Larmor frequency of the MRI scanner 1. If the radius R is less than the right-hand term, then the radio wave propagates exponentially attenuated in the patient tunnel 16 and the interference signal is heavily attenuated in the middle in the examination region FoV. Lambda$_L$ is also referred to as the limit wavelength of a round hollow conductor, and the associated frequency is referred to as the limit frequency.

Only the patient 100 acts through a finite conductivity as a core of a coaxial cable, the sheath of which is a wall of the patient tunnel 16, and passes on an electromagnetic signal coupled in at the legs or the top of the head into the examination region. A second receiving antenna 70 or second receiving antennas 70 arranged in the vicinity of the opening or in the patient couch 30 receive the interference signal passed on from the patient 100 into the FoV and thereby make the compensation in the receiver 70 especially effective.

Figure 2:
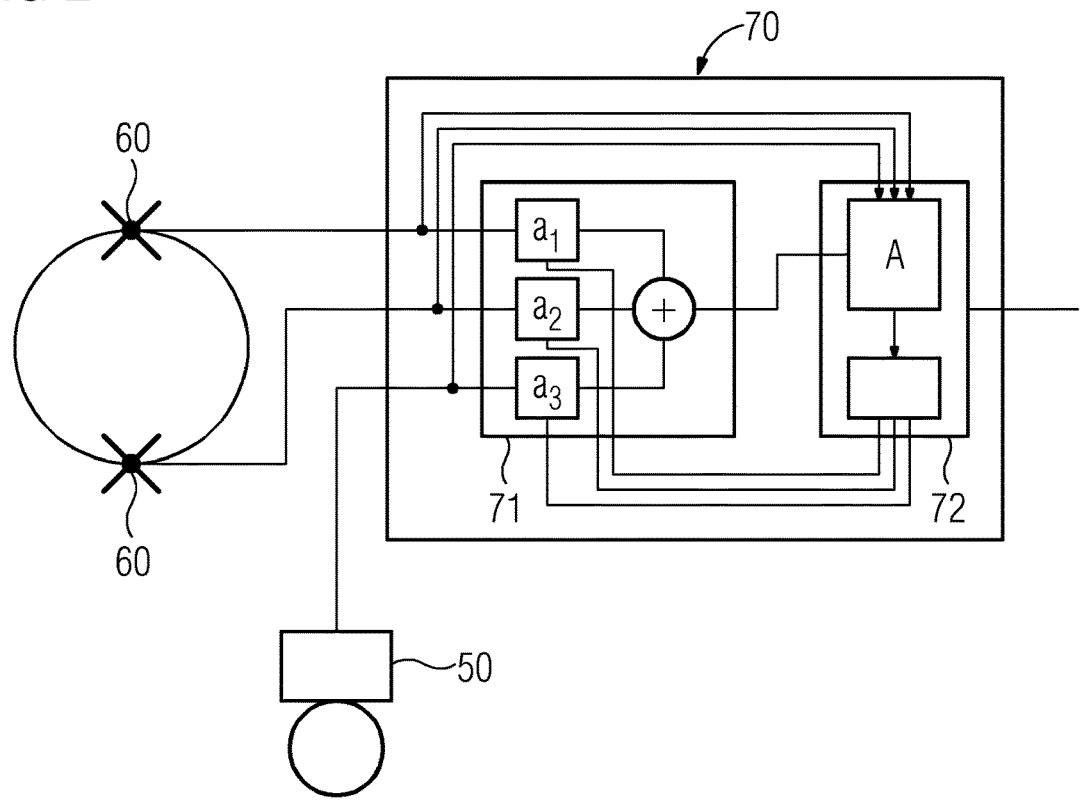
FIG. 2 shows a schematic diagram of a receiver, a first receiving antenna, and second receiving antennas according to an embodiment.

FIG. 2 shows a schematic diagram of the functional units of a possible form of embodiment of a receiver 70.

The summation device 71 weights the signals entering from the first receiving antenna or local coil 50 and from the second receiving antennas 60 with parameters, which may also be complex, in order to specify a phase displacement. In an analog receiver 70, this may take place by an adjustable amplifier in conjunction with an adjustable phase shifter. The real part of the parameter then corresponds to the amplification factor and the imaginary part of the phase displacement. Subsequently, in an embodiment, the weighted signals are summed, but other non-linear signal operations for combination of the individual signals may also be provided.

An interference suppression controller 72 receives the combined signal and also the individual signals of the first receiving antenna and the second receiving antennas 60. In order to determine a portion of the interference signal in the combined signal, the interference suppression controller 72 may, for example, undertake an autocorrelation of the signals. In one embodiment, however, the energy of the combined signals may be determined. In one embodiment, the interference suppression controller 72 determines the portion of the interference signal in sections of sequences of the MRI scanner in which no magnetic resonance signal for imaging is expected, so that the combined signal only has the interference signal. This may be the case, for example, in dephased sections of an echo sequence, since the amplitudes of individual nuclear spins cancel each other out because of different phase and do not generate any signal overall.

The interference suppression controller 72 then optimizes the parameters in the summation device according to a least square root (LSR) method, for example, so that the portion or the energy of the interference signal in the combined signal is minimized.

The receiver 70 may be configured both in analog signal processing technology, so that, for example, gain control and phase displacement are controlled by a parameter and then converted using analog means, or also as a digital receiver that either already receives digitized signals from the first receiving antenna and/or the second receiving antenna 60 or already digitizes the signals at the signal input by an A/D converter.

For imaging, the receiver 70 forwards the combined signal, in which the interference signal is very largely suppressed, to the controller 23 of the MRI scanner.

The bandwidth of the interference signal may be wider than the magnetic resonance signal. The portions outside the frequency range of the magnetic resonance signal usually correlate in this case with the portions within the frequency range of the magnetic resonance signal. Therefore, it may also be sufficient in accordance with the present embodiments for the second receiving antenna 60 to receive the wideband interference signal only in part (e.g., in a frequency range that is not the same as or is outside the frequency range of the magnetic resonance signal). In addition or as an alternative, the receiver 70 may also be configured only to accept frequencies in this frequency range from the second receiving antenna. The receiver 70 is configured in this case, depending on this part signal, to suppress the interference signal in a magnetic resonance signal received by the first receiving antenna. Because of the correlation, for example, the amplitude of the frequency components of the interference signal in the frequency range of the magnetic resonance signal may be linked with an amplitude outside the frequency range. In one embodiment, the second receiving antenna 60 in conjunction with the receiver 70 may only monitor frequency components outside the frequency range of the magnetic resonance signal for interference signals during an MRI scan and may suppress the interference signal in the signals of the first receiving antenna as a function thereof. In one embodiment, the receiver 70 may establish a relationship between the interference signal from the first receiving antenna and the interference signal portion from the second receiving antenna 60 (e.g., the transfer function) for an interference signal in the frequency range of the magnetic resonance signals between acquisitions of magnetic resonance signals and during the acquisition of magnetic resonance signal (e.g., to adapt the amplitude or scaling of received portions of the interference signal based on the second receiving antenna outside the frequency range of the magnetic resonance signal).

In another embodiment of the MRI scanner, the interference signal is not suppressed in the receive signal in real time (e.g., not immediately on receipt of the interference signal and/or of the magnetic resonance signal), but the magnetic resonance signal and the interference signal are stored by the receiver 70, which may also include parts of the controller 23 of the MRI scanner 1 or of an image evaluation unit, in a memory. The acts set out below for the method then no longer take place in real time or almost in real time, but may be carried out on the stored data with a delay (e.g., in advance of an image evaluation).

For example, a combination of receipt with the second antenna outside the frequency band of the MR signal with a real time interference suppression or a suppression at a separate point in time (e.g., during image evaluation) may be provided.

The interference suppression in the receiver shown in FIG. 2 may also be carried out with a single second antenna 60. In one embodiment, the receiver 70 may have a number of channels, or a number of receivers 70 may be provided in the MRI scanner 1 in order to suppress interference in the magnetic resonance signals of a number of local coils 50. The signals of the second receiving antennas 60 may be used by a number of receivers 70 or channels of the receiver 70 for interference suppression.

The dependence between the interference signal received by the second antenna and the interference suppression may be linear and also non-linear. Linear dependencies may be a phase displacement about a value determined or a linear scaling with a value determined from the signal of the second antenna. The transfer function for the interference signal may have non-linearities on the path from the first receiving antenna and/or second receiving antenna (e.g., through mixers or non-linear amplifiers), so that non-linear operations for interference suppression in the receiver 70 are also to be applied to the interference signal received by the second receiving antenna 60.

Figure 3:
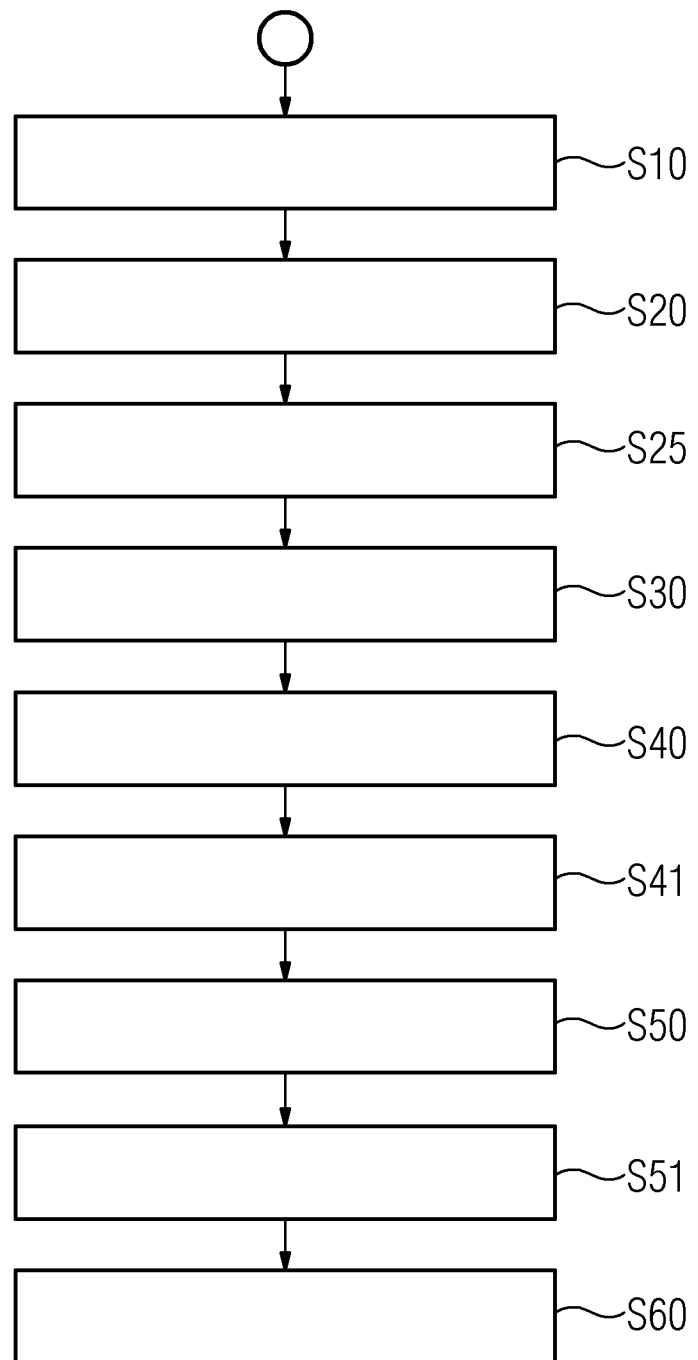
FIG. 3 shows a schematic diagram of a flowchart of a form of embodiment of a method.

FIG. 3 shows a schematic flowchart of one embodiment of a method.

In act S10, the receiver 70 receives an interference signal via the second receiving antenna 60 or via the plurality of second antennas 60. The interference signal is transmitted via a signal connection to the receiver 70. In this case, the interference signal may be digitized by an A/D converter (e.g., a digital receiver 70) before the interference signal is transmitted to the receiver 70.

In act S20, the receiver 70 receives a magnetic resonance signal via the first receiving antenna (e.g., the local coil 50). With a number of local coils 50, correspondingly more receivers 70 or also, one receiver 70 with a number of channels, each with a summation device 71, may be provided. The interference suppression controller 72 may be provided separately in each case or also jointly, which may speed up the subsequent setting or similar parameters for different channels.

In act S30, the receiver 70 processes the magnetic resonance signal as a function of the interference signal or the interference signals with a number of second receiving antennas 60 into one receive signal. For example, the interference signal or signals of the second receiving antenna or second receiving antennas 60 and the magnetic resonance signal of the first receiving antenna are weighted with different parameters and delayed and subsequently combined. This may be the creation of a linear combination, for example. The created receive signal or sum signal depends in this case on one or more parameters.

In another act S40, the parameter or the parameters are set by the receiver 70 (e.g., by the interference suppression controller 72) such that a portion of the interference signal in the receive signal is reduced. If, for example, the interference signal received by the second receiving antenna 60 is scaled by the parameters set so that the interference signal received by the second receiving antenna 60 has the same amplitude as the interference signal portion received via the first receiving antenna; if the interference signal received by the second receiving antenna 60 is provided with a phase displacement relative thereto of 180 degrees, then the interference signal in the created signal is exactly canceled out. The parameter or the parameters may be established in this case via optimization methods such as, for example, least square root (LSR) or Wiener filter.

The act S40 in this case may also have the sub-act S41 to form a temporal average value and to set the parameter for interference suppression as a function of this average value. For example, an amplitude or phase of the interference signal may be averaged in order to compensate for statistical fluctuations and introduce less interference into the magnetic resonance signal through the interference suppression.

In this case, the acts S10 to S30 may be carried out in each case on received magnetic resonance signals and received interference signals in real time (e.g., with analog receivers 70). However, the acts S10 to S30 may be carried out in each case on stored interference signals and magnetic resonance signals, which are digitized, for example, for an individual sequence or individual sections thereof.

In one embodiment of the method, the act S40 is carried out with interference signals from a period of a sequence in which no magnetic resonance signal for imaging is received. For example, the parameters may be determined with interference signals of the second receiving antenna 60 and a signal of the first receiving antenna in a time section of the interference suppression controller 72 in which the nuclear spins are dephased and create no magnetic resonance signal. It is also conceivable, however, in this time section, without magnetic resonance signal, for the interference signal and the signal of the first receiving antenna to just be acquired digitally and evaluated later.

In this case, in act S50, the interference suppression controller 72 may monitor the interference signal for changes (e.g., different amplitude, frequency, or phase). On detection of such a change or if the change exceeds a predetermined threshold value, the interference suppression controller 72 may modify the acts S10 of receipt of interference signal and S20 receipt of the magnetic resonance signal, as well as the setting of a parameter for interference suppression as a function of the received interference signal in act S51 in order to adapt the interference suppression to the changed interference signal.

In one embodiment of the method, the received interference signal and/or magnetic resonance signal may be stored by the receiver 70 in act S25. In this case, the receiver 70 may also include parts of the controller 23 of the MRI scanner 1 or an external image evaluation processor. The acts S20 to S40 are carried out retroactively in this case, for example, at the end of an echo sequence, an excitation sequence, a signal acquisition for a slice of the examination object, or also after acquisition of all data.

The decoupling of the signal acquisition from interference signal and magnetic resonance signal from the interference suppression thus make it possible in an advantageous way to employ lower-cost components with lower computing power or also to use existing resources (e.g., from the image evaluation) twice. In one embodiment, different parameter settings may be compared and selected, or the different parameter settings may be optimized retrospectively. The application may also be limited to periods of time with disruptions.

Figure 4:
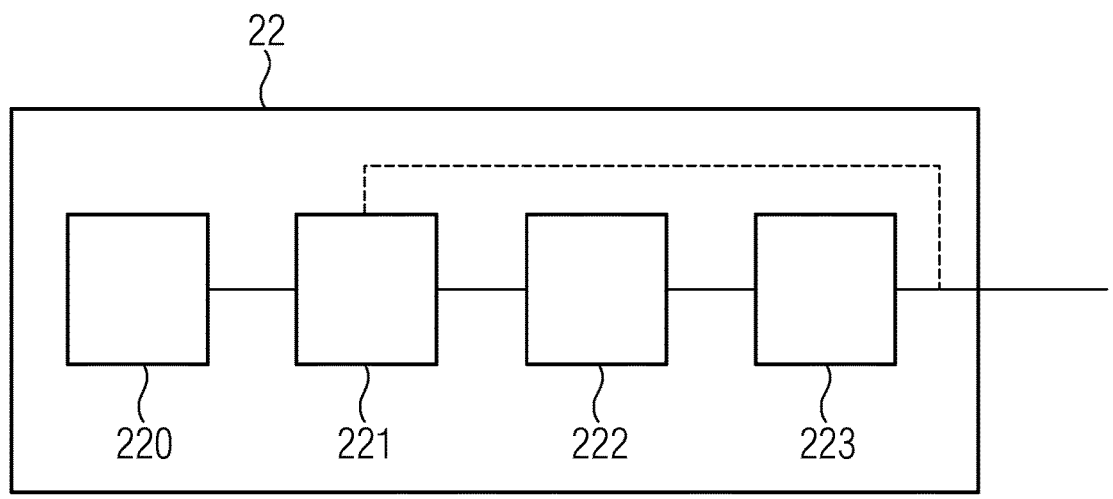
FIG. 4 shows a schematic diagram of a radio frequency unit of one embodiment of an MRI scanner.

FIG. 4 shows a schematic diagram of a radio frequency unit of one embodiment of an MRI scanner. The diagram in this case does not show all details of the radio frequency unit, but only the details relevant for an interference suppression on the transmit path of the present embodiments.

The transmit path of the radio frequency unit 22 in this case has a pulse generator 220, a preliminary interference suppressor 221, a power amplifier 222, and an ISM filter 223.

The pulse generator 220 may have an oscillator, a modulator, and a mixer, for example, with which a pulse generated in the baseband is then converted to the Larmor frequency.

The preliminary interference suppressor 221 is configured for preliminary interference suppression of an excitation pulse for excitation of the nuclear spins such that portions of the signal of the excitation pulse outside the ISM band are reduced compared to an excitation pulse without preliminary interference suppression. In one embodiment, preliminary interference suppressor 221 may create and mix-in signal portions that, after an amplification by the power amplifier, correspond to harmonics created by the non-linearity of the power amplifier from the excitation pulse, but have a reversed sign and in this way reduce or extinguish the harmonics. The same may be provided for intermodulations of signal portions by the non-linearity. The preliminary interference suppressor 221 in this case may be realized, for example, in a digital signal creation, or also, corresponding signals are created from an input signal for a power amplifier by analog components. In one embodiment, the preliminary interference suppressor 221 may be integrated in a digital pulse generator 220, for example.

The output signal of the preliminary interference suppressor 221 is amplified in the power amplifier 222. A power amplifier 22 with a linear characteristic curve may be provided. In one embodiment, the preliminary interference suppressor 222 may change the input signal of the power amplifier 222 such that, after amplification by the power amplifier 222, a signal is generated without unwanted harmonics. In other words, the characteristic curve of the preliminary interference suppressor 221 multiplied by the characteristic curve of the power amplifier 222 may give a linear characteristic curve, so that the system consisting of preliminary interference suppressor 221 and power amplifier 222 amplifies a pulse of the pulse generator without unwanted harmonics.

The preliminary interference suppressor 221, in one embodiment, as shown in FIG. 4 by the dashed line from the output of the ISM filter 223, may also be adaptive in the sense that, by monitoring the output signal of the power amplifier 222, the preliminary interference suppressor 221 adapts the preliminary interference suppression, so that the overall system, consisting of preliminary interference suppressor and power amplifier, has a linear characteristic.

Subsequent to the power amplifier 222, the signal may still be filtered by an ISM filter 223. The filter may suppress frequency components outside the ISM band that the MRI scanner 1 needs for image acquisition. For example, the filter may involve a bandpass filter for the ISM band used that attenuates frequencies outside the ISM band by more than 12 dB, 24 DB, 40 dB, or 60 dB relative to a signal with minimal attenuation within the ISM band. A lowpass is also possible. Depending on the radio frequency generation of the MRI scanner, the filter may be arranged, for example, between power amplifier 222 and a hybrid coupler not shown, between hybrid coupler and a transmit/receive switch not shown, or between transmit/receive switch and transmit antenna.

In one embodiment, the MRI scanner also has tuning elements for the transmit antenna. These may be PIN diodes, for example, but may also be other diodes or active components such as transistors or FETs. These tuning elements are provided in order to tune the transmit antenna in the case of receipt and to avoid interactions with the receiving antennas. The tuning elements usually having non-linear characteristic curves may therefore generate harmonics during transmission. In one embodiment, the ISM filter 223 is therefore arranged between the tuning elements and the transmit antenna. The non-linear components may also be arranged in an area of the MRI scanner screened off from the patient tunnel for radio frequency.

Thus, the arrangement of the non-linear components contributes to adherence to irradiation limit values and makes possible or simplifies dispensing with screening of the entire MRI scanner with a radio frequency cabin.

Figure 5:
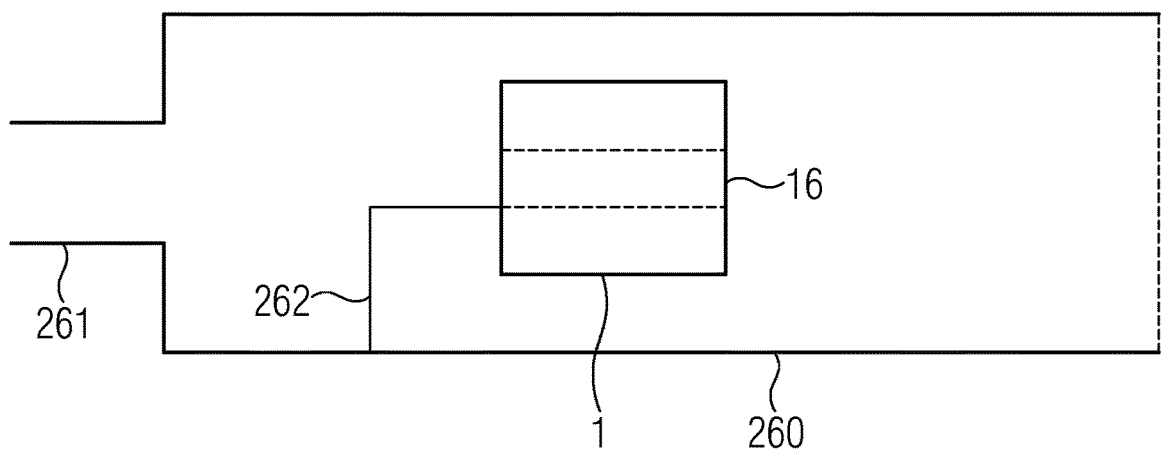
FIG. 5 shows a schematic diagram of one embodiment of an MRI scanner surrounded by a waveguide.

Shown schematically in FIG. 5 is an embodiment of an MRI scanner 1 surrounded by a waveguide. The waveguide 260 may be provided in this case by any electrically conductive surface surrounding the outer circumference of the MRI scanner 1 in at least four spatial directions. An electrically conductive surface is, for example, a metallic or metalized surface or mesh that attenuates an electromagnetic wave with the Larmor frequency at a crossing by 60 dB, 80 dB, 100 dB, or more. The conductivity of the surface may also be anisotropic through geometrical subdivision such as slots, provided the conductivity in parallel to the electrical field vector of the alternating field is sufficient to achieve the attenuation.

In one embodiment, the surface forms the waveguide 260 as a tunnel around the MRI scanner (e.g., in the form of a cylinder, cube, prism with a width that does not allow any formation of a free wave with Larmor frequency). With a cube, this is the case, for example, if the longer dimension of the cross section is less than a half wavelength of an electromagnetic wave with the Larmor frequency. In other words, the cut-off frequency or limit frequency of the waveguide 260 is greater than the Larmor frequency. The electromagnetic field thereby falls exponentially with the distance from the source, so that alternating fields leaking out of the patient tunnel 16 fall rapidly. In one embodiment, the waveguide 260 may be open at one or both ends, since the distance to the patient tunnel 16 provides that the exponential attenuation is already strong enough to adhere to the limit values allowed in the ISM band.

In one embodiment, the MRI scanner 1 may be surrounded by screening that has larger dimensions than the half wavelength. Then, however, instead of a radio-frequency-tight door, a tunnel-shaped access opening 261 made of conducting material with a correspondingly small cross section to the MRI scanner 1 may be provided. The dimensions of the tunnel-shaped access opening 261 suppress the free propagation of the wave by a cut-off frequency greater than the Larmor frequency. The access opening 261 may be connected electrically-conductively for radio frequency with the screening and/or the waveguide. In an embodiment, the waveguide 260 is also connected electrically-conductively to the patient tunnel 16 for radio frequency.

Figure 6:
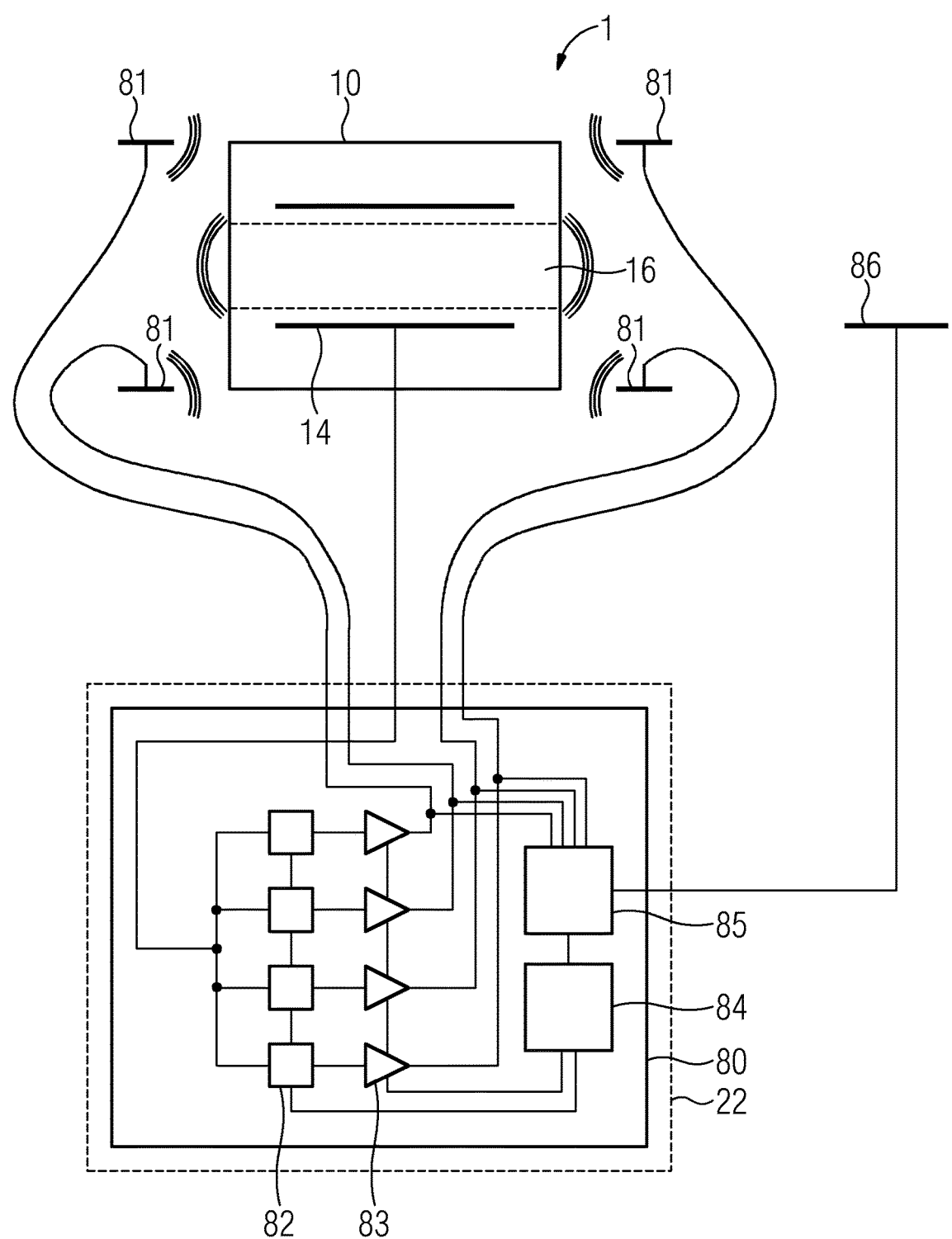
FIG. 6 shows a schematic diagram of one embodiment of an MRI scanner with an interference suppression transmitter.

FIG. 6 shows a schematic diagram of an embodiment of an MRI scanner 1 with an interference suppression transmitter 80. Electrical waves or alternating waves are also able to be suppressed by electrical fields with the same frequency and amplitude amount but opposite polarity or a phase displacement by 180 degrees. If amplitude amounts or phase do not match exactly, then at least a reduction by the destructive interference is achieved. One embodiment of an MRI scanner 1 has interference suppression antennas 81 for creating these alternating fields for interference suppression, which are arranged around the source of the fields (e.g., around the patient tunnel 16). In one embodiment, the interference suppression antennas 81 cover all spatial directions around the opening and a symmetry is used, such as, for example, the same distances to the opening of the patient tunnel 16 and/or a distribution at the same angular distances to the opening in order to simplify an activation of the individual interference suppression antennas 81. Through amplitude and phase able to be set individually for each interference suppression antenna 81, however, any given distribution may be provided. Depending on the type of the alternating field, antennas with, for example, an electrical field such as, for example, dipoles or with a magnetic field such as, for example, transmit coils may also be involved. The alignment of the antennas or the polarization of the field generated in this case may be oriented to the field direction of the alternating fields to be suppressed.

The signal that is transmitted from the interference suppression antennas 81 is intended to reduce the emission of the excitation pulse and is thus to have a predetermined amplitude and phase relationship to the excitation pulse. In one embodiment, the signals are therefore derived as analog signals or also from the digital pulse generation. In one embodiment, the signals may be provided through separate units independently of the pulse generation, provided the necessary amplitude and phase relationship is established.

In FIG. 6, a connecting line between the body coil 14 as source of the electromagnetic waves and the interference suppression transmitter is specified symbolically. A direct connection via a power distributor or, for example, a directional coupler may be provided; a sensor in the patient tunnel may also be possible for direct acquisition of the electromagnetic field. In one embodiment, a reference signal for creating the signal for interference suppression may be obtained from the power amplifier 222 or the pulse generator 220.

The reference signal for interference suppression derived from the excitation pulse is subsequently delayed or phase-shifted by adjustable phase shifters 82 for the individual interference suppression antennas 81 and subsequently has an amplitude of the reference signal amplified by adjustable amplifiers 83, before the reference signal is transmitted via the interference suppression antennas 81.

The phase shifters 82 and the amplifiers 83 are adjusted in this case by an interference suppression controller 84 via a signal connection. In one embodiment, the interference suppression controller 84 may set predetermined phase shifts and amplitudes, which are established, for example, during the installation of the MRI scanner 1.

In one embodiment, the adjustment may take place by a calibration measurement. In this case, a calibration receiver 85 may record the alternating field to be suppressed by one or more calibration elements 86 distributed in the room. At the same time, the calibration receiver 85 acquires the signals supplied to the interference suppression antennas 81 and transfers the acquired values to the interference suppression controller 84. The interference suppression controller 84 may then, for example, adjust the interference suppression controller 84 by a linear optimization method such as LSR of the phases and amplitudes of the individual interference suppression antennas, such that, at the location of the calibration antennas 86, the field strength is zero. If the n calibration elements 86 are distributed across the spatial angle, then the resulting alternating field from body coil 14 and interference suppression antennas 81 may be changed to a multipole field with n zero points or radiation areas that decrease at a higher power with distance and make an effective suppression possible.

In this case, the propagation of the fields is reversible. For calibration, the calibration element or elements 86 may transmit a signal, and the body coil 14 and the interference suppression antennas 84 may receive the signal; then, the interference suppression controller 84 may establish a suitable phase relationship and amplitudes.

The calibration element 86 may also be used for transmitting a reference signal for receive interference suppression. In this case, the reference signal may have to be encoded or modulated so that the reference signal is able to be distinguished from a magnetic resonance signal by the receiver 70. This may, for example, also be achieved below the interference limit of the magnetic resonance signal with a spread-spectrum modulation. In one embodiment, a transmission in an adjacent frequency range may be provided. In this case, i the receiver 70 may be able to establish a correlation between the reference signal and the signals received via the second and first receiving antennas in order to optimize the interference suppression. In this way, settings for suppression of interference signals from specific directions may be determined, for example.

Figure 7:
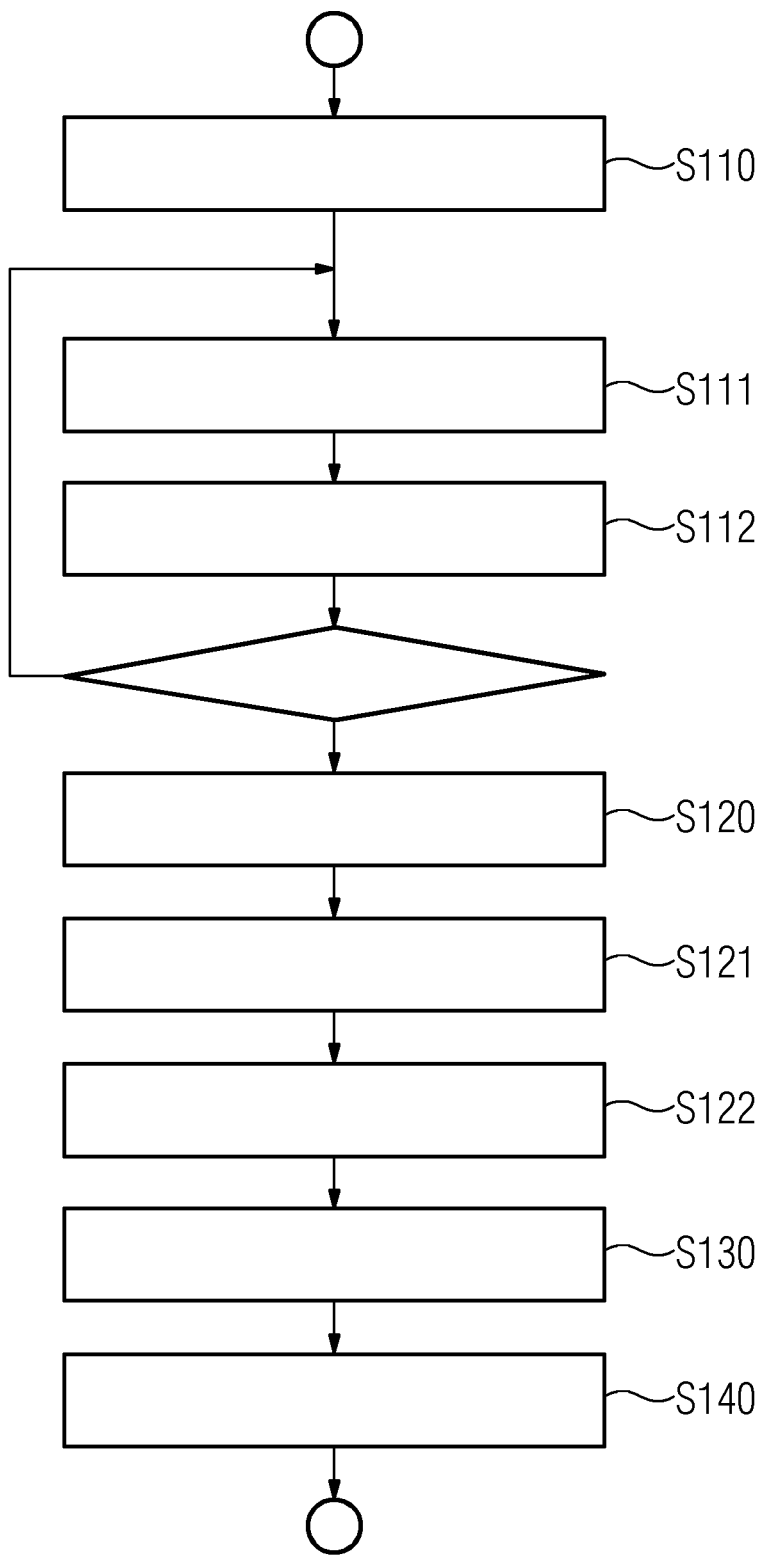
FIG. 7 shows a schematic diagram of a flowchart of a part aspect of one embodiment of a method.

FIG. 7 shows a schematic of a flowchart of a possible form of embodiment of a method. In FIG. 7, the aspect of how an excitation pulse is to be configured and transmitted is considered, for example, in order to adhere to regulatory limit values for radio frequency radiation even without a screening cabin (e.g., when the Larmor frequency lies in an ISM band). The acts of the method already explained in FIG. 3 are summarized in FIG. 7 under act S130 and are not explained once again. However, it is basically also possible to implement the measures explained for FIG. 7 for limiting emission during the excitation pulse even without the receive interference suppression from FIG. 3.

In act S110, an excitation pulse for excitation of nuclear spins in an examination object is determined by the controller 23. To do this, first of all, in act S111, an excitation pulse for excitation of the nuclear spins in a slice of the examination object is established by the controller 23. This may take place, for example, as a function of the selected sequence or type of examination by selecting from a library of excitation pulses. The frequency, the duration, the power, and the spectral distribution in this case depend on a number of parameters. The mid frequency is produced from the nuclear spins to be acquired, the strength of the homogeneous static magnetic field BO, the location of the slice in relation to the gradient field, and also the strength of the gradient field. The spectral distribution and bandwidth is produced from the strength of the gradient field and the thickness of the slice in the direction of the field gradients. The amplitude depends on the duration of the excitation pulse, the volume to be excited, and the desired excitation strength (e.g., the flip angle). In this case, in sub-act S111, a set of parameters is determined as a function of these boundary conditions, which describe a possible excitation pulse for these boundary conditions. In one embodiment, a library or table of different sets of parameters may be specified for specific standard situations, such as, for example, acquiring images of specific organs, and the set of parameters may be selected from the library or table.

In a further sub-act S112, a check is performed by the controller 23 as to whether the established excitation pulse lies within the predetermined frequency limits. In the simplest case, the highest and the lowest frequency of the excitation pulse may be computed, for example, with the aid of the mid frequency and the spectral frequency distribution. In one embodiment, the power distribution may be computed, and limit values for a frequency-dependent power may be assessed.

The sub-act S111 is repeated if it is determined in the assessment that the established excitation pulse exceeds limit values (e.g., limit values for an allowable emission of radio frequency power). This relates above all during operation of the MRI scanner in an ISM band to an emission outside the ISM band that is subject to greater restrictions.

In this case, parameters that influence this are varied on repetition of sub-act S111. A longer pulse may achieve the same excitation with a lower power, for example. With a smaller gradient, a smaller frequency bandwidth is required in order to excite the same slice thickness.

If the excitation pulse established in sub-act S111 adheres to the limit values, then the excitation pulse is transmitted in act S120 of the method by the radio frequency unit 22.

In act S130, as already described for FIG. 3, in an exemplary form of embodiment, the magnetic resonance signal is received by the receiver 70.

Subsequently, in act S140, a map of a distribution of nuclear spins by the controller 23 from the received magnetic resonance signal is established. In one embodiment, the mapping is finally reproduced on a display.

Figure 8:
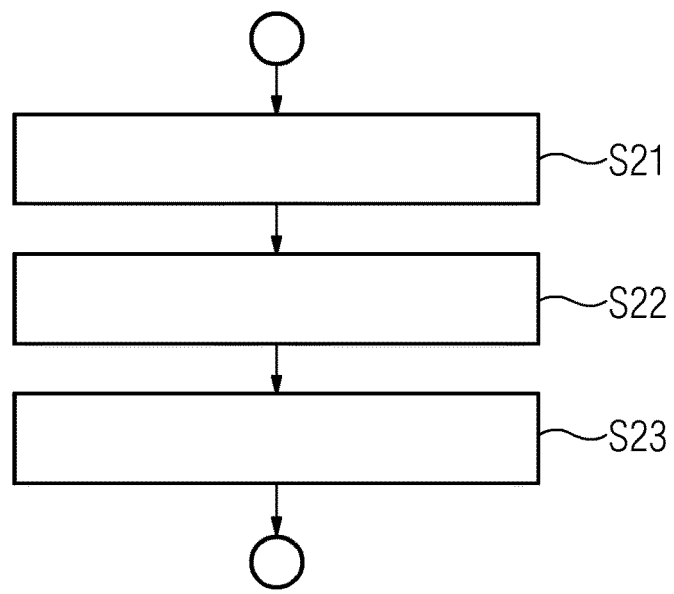
FIG. 8 shows a schematic diagram of a flowchart of a part aspect of one embodiment of a method.

FIG. 8 shows a schematic of a flowchart of a further sub aspect of the method shown in FIG. 3 (e.g., a possible interference suppression by previously acquired image information).

In this case, the receiver 70 receives in act S21 a first received magnetic resonance signal and stores the first received magnetic resonance signal in a memory. In this case, it the signal acquired in act S21 may originate from a calibration measurement or a pre-scan that has also been acquired with other parameters or a lower resolution.

In a further act S22, the receiver 70 receives a second received magnetic resonance signal and stores the second received magnetic resonance signal. In one embodiment, the second magnetic resonance signal involves a signal for an image acquisition.

In act S23, the first received magnetic resonance signal and the second received magnetic resonance signal are compared. This may already take place in the raw data, for example, or not until the image space (e.g., after a Fourier transform). In one embodiment, the comparison is undertaken on a row basis in the k-space. If the first magnetic resonance signal and the second magnetic resonance signal differ significantly (e.g., if a possibly different recording situation has already been taken into consideration in the comparison), then with a deviation that is to be attributed to external interference, an interference suppression measure is performed. Interference signals may be characterized by the frequency, amplitude, or a characteristic curve or duration, for example.

An interference suppression measure in this case may be a repetition of the acquisition, for example, that (e.g., for a row in the k-space) leads to shorter delays. In one embodiment, the signal may be set to zero (e.g., if involving a region from which no image signal is to be expected).

Figure 9:
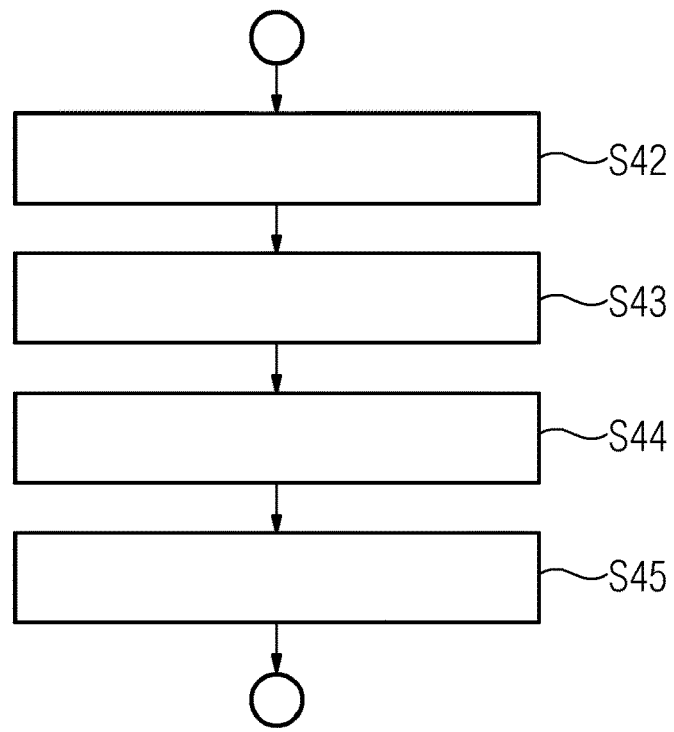
FIG. 9 shows a schematic diagram of a flowchart of a part aspect of one embodiment of a method.

FIG. 9 shows a schematic of a flowchart of a further sub aspect of one embodiment of a method for interference suppression (e.g., a possible interference suppression by analysis of the acquired image information in an image space).

In this possible form of embodiment of the method, the magnetic resonance signal is investigated in the image space to detect the interference signal and to define the parameters for interference suppression. To do this, in a sub-act S42, the received magnetic resonance signals are transformed by the controller 23 in an image space (e.g., by a Fourier transform). This act may also be performed like the subsequent acts on individual rows of the raw data space, so that a detection and correction may be performed more quickly.

In another sub-act S43, the interference signals are separated by the controller 23 from the magnetic resonance data. This is possible, for example, if regions in the image space may be determined by a segmentation from a pre-scan or other additional information about patient and location, at which no magnetic resonance signals from nuclear spins are to be expected. Signals arising there in the image space are then to be assigned to a disruption.

In a further sub-act S44, the interference signals are transformed back into a raw data space (e.g., by a further Fourier transform).

In another sub-act S45, the parameters for interference suppression may then be determined from the interference signals separated from the useful signal and transformed back in the raw data space (e/g/. as phase and amplitude for destructive interference in the receiver from the signals of the first and second receiving antennas). In one embodiment, the acts of back transformation and the determination of parameters may be linked to one another, since frequency and phase in the raw data space are linked to the position in the image space.

Figure 10:
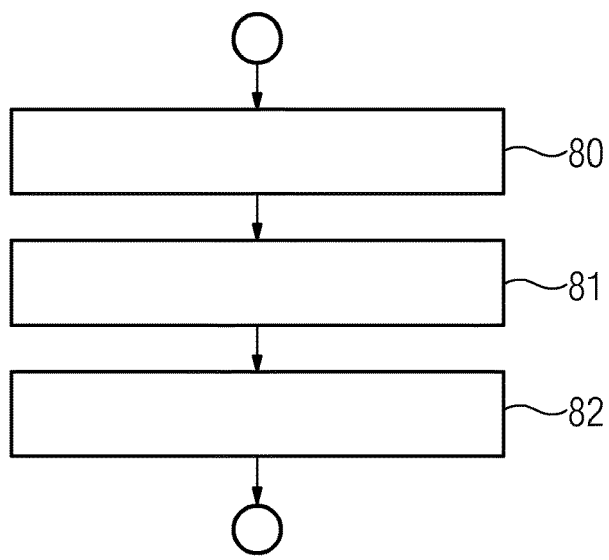
FIG. 10 shows a schematic diagram of a flowchart of a part aspect of one embodiment of a method.

FIG. 10 shows a schematic of a flowchart of a further sub aspect of one embodiment of a method for interference suppression, which establishes transfer functions between first receiving antennas and second receiving antennas 60 with one or more additional calibration elements 86.

In a sub-act S80 in this case, a transfer function between a first receiving antenna and the calibration element 86 is established. For this, a signal may be transmitted by the interference suppression controller via the calibration element 86 with the coordination of controller 23, which is received and evaluated by the first receiving antenna. In one embodiment, the signal is encoded by pseudo random sequence or in another way such that a correlation between sent and received signal may be easily established by the receiver 70.

In a sub-act S82, a transfer function between a first receiving antenna and the calibration element 86 is established in the same way. For this, it a signal may be transmitted via the calibration element 86 with the coordination of the controller 23 by the interference suppression controller, which is received by the second receiving antenna 60 and is evaluated in the receiver 70.

On account of the reversibility of the propagation of the electromagnetic fields, signals may also be sent however by the first receiving antenna and the second receiving antenna 62, which will be received by the calibration element 86.

In another sub-act S82, at least one parameter for interference suppression as a function of the measured transfer functions is set such that a portion of an interference signal received by the second receiving antenna 60 is reduced in a signal received by the receiver 70 via the first receiving antenna. For example, the at least one parameter may be defined in each case via the transfer functions how an interference signal arrives from the direction of the calibration element 86 at the input of the receiver 70 via the first receiving antenna and the second receiving antenna 60 (e.g., with which amplitude and phase displacement). Thus, for example, an additional phase displacement may be set in receiver 70, so that the signals from first receiving antenna and second receiving antenna are superimposed destructively in the receiver and the fault is suppressed. As a further parameter, the amplification of the amplitude may be set so that there is an extinction for an interference signal from a point in space. With a number of first receiving antennas and second receiving antennas 60, more parameters or pairs of parameters are to be adapted accordingly, which may take place, for example, by linear optimization methods such as LSR.

Figure 11:
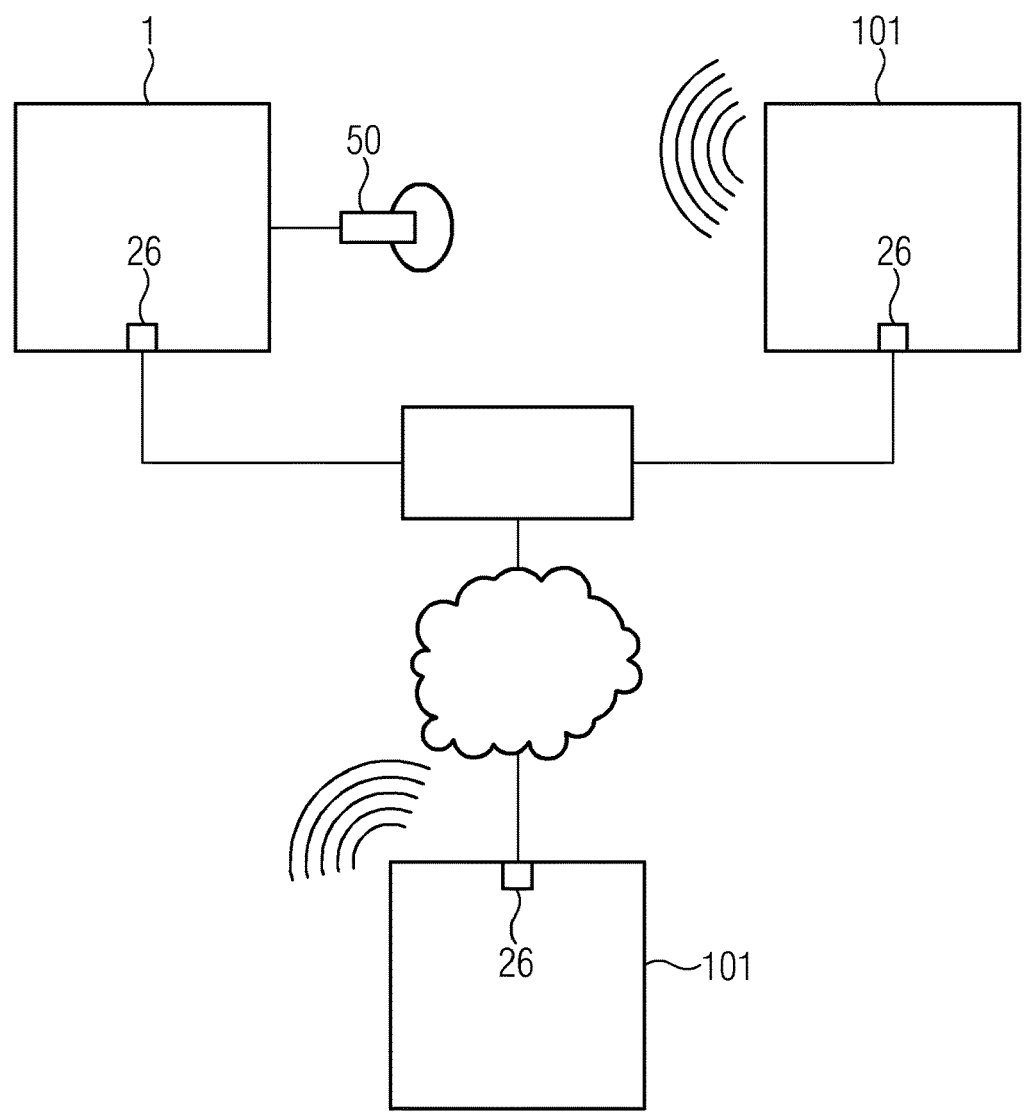
FIG. 11 shows a schematic diagram of one embodiment of an MRI scanner, in a network with further MRI scanners.

Shown in FIG. 11 is an interaction between a number of MRI scanners 1 of the present embodiments. In this case, the control unit 20 of the first MRI scanner 1 receives a signal from a second MRI scanner 101 via an interface. The control unit 21 in this case is configured to synchronize an image acquisition as a function of a signal received via the interface from the second MRI scanner.

A number of possible forms of embodiment are shown simultaneously in FIG. 11. The interface may be the LAN interface 26, via which the MRI scanner 1 is connected to the second MRI scanner 101 for signaling. In one embodiment, all other interfaces for the exchange of information such as WIFI, WAN, or serial or parallel point-to-point-connections may be provided.

In a form of embodiment, the second MRI scanner 101 may transmit a message about a planned image acquisition with the signal. The message may, for example, specify that at a specific time t, at the frequency f, an excitation pulse of duration d will be sent by the second MRI scanner 101. The control unit 20 of the first MRI scanner 1 then synchronizes an own image acquisition as a function of this information.

One possibility is for the control unit 20 to synchronize an own excitation pulse such that the excitation pulse occurs at the same time, since because of the extremely high field strengths that are required for excitation, the excitation pulses of adjacent MRI scanners, because of the attenuation already provided by the construction of the MRI scanners, do not disrupt one another.

More sensitive to disruptions is the receipt of magnetic resonance signals from the examination volume or the patient 100. Since an attenuation in relation to the excitation pulse of over 100 dB is present, an excitation pulse of an adjacent MRI scanner 101 may disrupt the receipt of MR signals even when screening is present. The control unit 20 of the MRI scanner 1 may therefore plan and carry out the image acquisition such that this does not coincide with the excitation pulse of the second MRI scanner 101. For example, own excitation pulses and the readout sequences dependent thereon may be applied so that the receipt windows of the first MRI scanner 1 do not coincide with the excitation pulses of the second MRI scanner 101.

In this case, it is also conversely possible for the second MRI scanner 101 to transmit information about a planned receipt. The message may, for example, specify that at a specific time t, at the frequency f for the duration d, an MR signal is to be recorded by the second MRI scanner 101. The first MRI scanner 1 may then set an own transmission process so that no transmission process takes place in the time window specified in the message, at least not on a frequency band that includes the frequency f including a bandwidth specified in the message.

Combined messages, in which transmit and receive processes are agreed mutually between the first MRI scanner 1 and the second MRI scanner 101 (e.g., such that the image acquisition devices may be executed with the least possible delay by interleaving), may also be provided.

In another form of embodiment, which is shown in FIG. 11, the signal may, however, be a radio wave of an excitation pulse itself, and the interface may, for example, be the local coil 50 with the radio frequency unit 22. In one embodiment, receipt also or just takes place at times at which the first MRI scanner 1 is not itself recording an MR signal. Based on the excitation pulse, the control unit 20 may detect that a second MRI scanner 101 has just transmitted an excitation pulse and therefore is then planning an acquisition of a magnetic resonance. It is then, for example, possible for the first MRI scanner 1 then not to transmit any excitation pulse itself for a certain time. The first MRI scanner 1 may use the excitation pulse of the second MRI scanner 101 itself as a trigger pulse and may transmit the own excitation pulse almost synchronously, since usually pauses without receipt and thus possible mutual interference lie between excitation pulse and receipt of the magnetic resonance signal.

Regardless of whether the transmission of an excitation pulse is detected directly via the received electromagnetic field of the pulse or via a message via the data interface, the control unit 20 may change the frequency of the next excitation pulse as a function of the signal. In MRI scanning, individual slices in the direction of the BO field, usually along the z-axis 2, are differentiated by a superimposed gradient field in the z direction in frequency and are thus able to be distinguished. The control unit 20 may, for example, change the order of the scanning of individual slices, so that the first MRI scanner 1 and the second MRI scanner 101 each acquire slices with different mid frequency, and in this way, crosstalk or interaction are avoided by the different frequencies. An additional degree of freedom that the control unit 20 may use in this case is also the location of the patient 100 on the movable patient couch 30 relative to the isocenter of the field magnet 10. By moving the patient 100 along the z-axis a little, the different location in relation to the z gradient field provides that the Larmor frequency also changes for a slice. The first MRI scanner 1 may thus, by a relative movement of the patient along the z-axis, also acquire the same slice in the body of the patient 100 with different frequencies, so that an interaction with the second MRI scanner 101 may be avoided.

Although the invention has been illustrated in greater detail by the exemplary embodiments, the invention is not restricted by the disclosed examples, and other variations may be derived herefrom by the person skilled in the art, without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance imaging (MRI) scanner comprising:
   a patient tunnel;
   a first receiving antenna operable to receive a magnetic resonance signal from a patient in the patient tunnel;
   a second receiving antenna operable to receive a signal having the Larmor frequency of the magnetic resonance signal; and
   a receiver,
   wherein the second receiving antenna is arranged outside or in a vicinity of an opening of the patient tunnel,
   wherein the receiver is connected to the first receiving antenna and the second receiving antenna for signaling, and the receiver is configured to suppress an interference signal received with the second receiving antenna in a magnetic resonance signal received by the first receiving antenna, and
   wherein the MRI scanner is configured to receive magnetic resonance signals having a Larmor frequency in an industrial band.

2. The MRI scanner of claim 1, wherein the MRI scanner has a transmit path for transmitting an excitation pulse with an ISM filter, and
   wherein the ISM filter is configured to suppress signals outside the ISM band.

3. The MRI scanner of claim 2, further comprising a transmit antenna for transmitting an excitation pulse,
   wherein the MRI scanner has non-linear components for tuning the transmit antenna,
   wherein the non-linear components are arranged in an area of the MRI scanner screened off for radio frequency from the patient tunnel, and
   wherein the ISM filter is arranged between non-linear component and antenna.

4. The MRI scanner of claim 1, further comprising a radio frequency unit,
   wherein the radio frequency unit has a preliminary interference suppressor configured for preliminary interference suppression of an excitation pulse for excitation of nuclear spins such that signal portions of the excitation pulse outside the ISM band are reduced compared to an excitation pulse without preliminary interference suppression.

5. The MRI scanner of claim 1, wherein a limit frequency for a propagation of a radio wave in the patient tunnel is greater than a Larmor frequency of the MRI scanner.

6. The MRI scanner of claim 1, further comprising a waveguide that surrounds the MRI scanner, and
   wherein the waveguide has a limit frequency that is greater than the Larmor frequency of the MRI scanner.

7. The MRI scanner of claim 6, wherein the waveguide has an electrically conductive connection to the patient tunnel.

8. The MRI scanner of claim 1, wherein the second receiving antenna is arranged on an opening of the patient tunnel or on the patient couch.

9. The MRI scanner of claim 1, wherein the second receiving antenna has an omnidirectional receive characteristic.

10. The MRI scanner of claim 1, further comprising additional second receiving antennas,
    wherein the receiver is configured to suppress the interference signal in the magnetic resonance signal as a function of receive signals of the second receiving antenna and the additional second receiving antennas.

11. The MRI scanner of claim 10, wherein the second receiving antenna and the additional second receiving antennas are arranged in an arrangement symmetrical to the patient tunnel.

12. The MRI scanner of claim 1, wherein the receiver has an autocorrelation device, and the autocorrelation device is configured to determine a portion of the signal received by the second receiving antenna in the magnetic resonance signal received by the first receiving antenna.

13. The MRI scanner of claim 1, wherein the receiver has an estimation device, and the estimation device is configured to estimate a portion of the signal received by the second receiving antenna in the magnetic resonance signal received by the first receiving antenna.

14. The MRI scanner of claim 1, further comprising:
    an interference suppression transmitter; and
    an interference suppression antenna,
    wherein the interference suppression antenna is arranged at a distance from the patient tunnel,
    wherein the interference suppression transmitter is configured to output a signal in a frequency range of an excitation pulse of the MRI scanner via the interference suppression antenna as a function of a transmit interference suppression parameter so that, in a predetermined area of an environment of the MRI scanner, a field strength of the excitation pulse is reduced by destructive interference.

15. The MRI scanner of claim 14, further comprising:
    a calibration element in an environment of the MRI scanner: and
    an interference suppression controller,
    wherein the interference suppression controller is configured to:
      detect a field strength in a frequency range of an excitation pulse at a location of the calibration element using the calibration element; and
      as a function of the detected field strength, set the transmit interference suppression parameter such that a field strength of the excitation pulse is reduced in a predetermined environment of the calibration element.

16. The MRI scanner of claim 14, wherein the interference suppression transmitter is configured to generate signals for the interference suppression antenna or interference suppression antennas by phase displacement, amplitude adaptation, or phase displacement and amplitude adaptation as a function of one or more transmit interference suppression parameters.

17. The MRI scanner of claim 14, wherein the interference suppression antenna has a radio frequency power amplifier.

18. The MRI scanner of claim 1, further comprising a calibration element in an environment of the MRI scanner,
    wherein the receiver is configured to:
      measure a first transfer function between the first receiving antenna and the calibration element and also a second transfer function between the second receiving antenna and the calibration element; and
      as a function of the measured first transfer function and the measured second transfer functions, set an interference suppression parameter or interference suppression parameters such that an interference signal received with the second receiving antenna is reduced in a magnetic resonance signal received by the first receiving antenna.

19. The MRI scanner of claim 1, further comprising:
a controller configured to control the image acquisition; and
an interface connected to the controller for signaling,
wherein the controller is configured to synchronize an image acquisition as a function of a signal received via the interface from a second MRI scanner.

20. The MRI scanner of claim 1, further comprising:
a controller configured to control the image acquisition; and
an interface connected to the controller for signaling,
wherein the controller is configured to transmit a signal with information about an impending image acquisition to a second MRI scanner.

21. The MRI scanner of claim 20, wherein the interface is configured for the exchange of data, and
wherein the controller is configured, using information exchanged via the interface, to synchronize an image acquisition with the second MRI scanner.

22. The MRI scanner of claim 20, wherein the signal has information about a time, frequency, or time and frequency of a transmission process.

23. The MRI scanner of claim 20, wherein the signal has information about a time, frequency, or time and frequency of a receive process.

24. A magnetic resonance imaging (MRI) scanner comprising:
a patient tunnel;
a first receiving antenna operable to receive a magnetic resonance signal from a patient in the patient tunnel;
a second receiving antenna operable to receive a signal close to the Larmor frequency of the magnetic resonance signal; and
a receiver,
wherein the second receiving antenna is arranged outside or in a vicinity of an opening of the patient tunnel,
wherein the receiver is connected to the first receiving antenna and the second receiving antenna for signaling, and the receiver is configured to suppress a wideband interference signal received with the second receiving antenna outside a frequency range of the magnetic resonance signal in a magnetic resonance signal received by the first receiving antenna,
wherein the MRI scanner is configured to receive magnetic resonance signals having a Larmor frequency in an industrial band.

25. A method for operation of an MRI scanner, wherein the MRI scanner has a patient tunnel, a first receiving antenna for receiving a magnetic resonance signal from a patient in the patient tunnel, a second receiving antenna for receiving a signal with the Larmor frequency of the magnetic resonance signal, and a receiver, wherein the second receiving antenna is arranged outside the patient tunnel or in a vicinity of an opening of the patient tunnel, the method comprising:
receiving an interference signal by the receiver via the second receiving antenna;
receiving a magnetic resonance signal by the receiver via the first receiving antenna;
processing the magnetic resonance signal as a function of the interference signal by the receiver to a receive signal, wherein a dependency is a function of a parameter; and
setting the parameter by the receiver, so that a portion of the interference signal is reduced in the receive signal,
wherein the MRI scanner is configured to receive magnetic resonance signals having a Larmor frequency in an industrial band.

26. The method of claim 25, wherein the MRI scanner has a Larmor frequency in an ISM band,
wherein the method further comprises:
determining an excitation pulse for excitation of nuclear spins in an examination object;
transmitting the excitation pulse; and
determining a mapping of a distribution of nuclear spins in the examination object based on the received magnetic resonance signal, and
wherein the excitation pulse is determined as a function of predetermined frequency limits of the ISM band.

27. The method of claim 26, wherein determining the excitation pulses comprises:
establishing an excitation pulse for exciting nuclear spins in a slice of the examination object as a function of a position of the slice relative to a magnet unit, a predetermined gradient strength, a thickness of the slice, and a type of measurement;
checking whether the established excitation pulse lies within the predetermined frequency limits of the ISM band;
repeating the establishing while varying a pulse parameter, which on establishing of the excitation pulse, has an effect on a spectral frequency distribution of the excitation pulse when the excitation pulse does not lie within the predetermined frequency limits or transmitting the established excitation pulse.

28. The method of claim 27, wherein the pulse parameter that affects the establishing of the excitation pulse is duration of the excitation pulse, thickness of the slice, relative position of the slice, or strength of the gradients.

29. The method of claim 26, wherein transmitting the established excitation pulse comprises changing a position of the examination object relative to the magnet unit before emitting the pulse.

30. A method for operation of a magnetic resonance imaging (MRI) scanner, wherein the MRI scanner has a patient tunnel, a first receiving antenna for receiving a magnetic resonance signal from a patient in the patient tunnel, a second receiving antenna for receiving a signal close to the Larmor frequency of the magnetic resonance signal, and a receiver, wherein the second receiving antenna is arranged outside the patient tunnel or in a vicinity of an opening of the patient tunnel, the method comprising:
receiving a frequency portion of the interference signal close to the Larmor frequency by the receiver via the second receiving antenna;
receiving a magnetic resonance signal by the receiver via the first receiving antenna;
processing the magnetic resonance signal as a function of the frequency portion of the interference signal by the receiver to a receive signal, wherein a dependency is a function of a parameter; and
setting the parameter by the receiver, so that a portion of the interference signal is reduced in the receive signal,
wherein the MRI scanner is configured to receive magnetic resonance signals having a Larmor frequency in an industrial band.

31. The method of claim 30, wherein setting the parameter comprises temporal averaging with formation of a temporal average value as a function of the interference signal.

32. The method of claim 30, wherein the MRI scanner further comprises a calibration element in an environment of the MRI scanner, and wherein the method further comprises:
measuring a transfer function between the first receiving antenna and the calibration element;
measuring a transfer function between the second receiving antenna and the calibration element;
setting the parameter as a function of the measured transfer functions such that a portion of an interference signal received by the second receiving antenna is reduced in a signal received by the receiver via the first receiving antenna.

33. The method of claim 30, wherein receiving the frequency portion of the interference signal comprises receiving the frequency portion of the interference signal at a time of a sequence at which no magnetic resonance signal for imaging is being received.

34. The method of claim 30, wherein the receiver has a memory,
wherein the method further comprises storing, by the receiver, the interference signal as well as the magnetic resonance signal in the memory, and
wherein the processing is undertaken with a delay relative to the receipt of the interference signal, the magnetic resonance signal, or the interference signal and the magnetic resonance signal.

35. The method of claim 30, wherein the receiver has an autocorrelation device, and
wherein setting the parameter comprises determining, by the autocorrelation device, a portion of the interference signal in the magnetic resonance signal and setting the parameter as a function of the portion of the interference signal determined.

36. The method of claim 30, wherein the receiver has an estimation device, and
wherein setting the parameter comprises determining, by the estimation device, a portion of the interference signal in the magnetic resonance signal and setting the parameter as a function of the portion of the interference signal determined.

37. The method of claim 30, wherein setting the parameter comprises:
transforming the received magnetic resonance signals into an image space;
separating the interference signals from the magnetic resonance signals;
transforming the interference signals into a raw data space; and
determining the parameters from the transformed interference signals in the raw data space.

38. The method of claim 37, wherein the transforming of the received magnetic resonance signals, the separating, the transforming of the interference signals, and the determining of the parameter are undertaken on rows of data of the received magnetic resonance signals in the raw data space.

39. The method of claim 30, further comprising:
monitoring, by the receiver, the interference signal for changes; and
adapting the parameter when there is a change.

40. The method of claim 30, further comprising:
storing, by the receiver, a first received magnetic resonance signal in a memory;
storing a second received magnetic resonance signal in the memory; and
comparing the first received magnetic resonance signal and the second received magnetic resonance signal and when there is a deviation that is attributable to external interference, performing an interference suppression measure.

41. The method of claim 40, wherein the interference suppression measure is a discarding of the first received magnetic resonance signal, the second received magnetic resonance signal, or the first received magnetic resonance signal and the second received magnetic resonance signal, a repetition of the acquisition of the first magnetic resonance signal, the second magnetic resonance signal, or the first magnetic resonance signal and the second magnetic resonance signal, or the setting of the parameter.

42. A method for operation of a magnetic resonance imaging (MRI) scanner, wherein the MRI scanner has a patient tunnel, a first receiving antenna for receiving a magnetic resonance signal from a patient in the patient tunnel, a second receiving antenna for receiving a signal having the Larmor frequency of the magnetic resonance signal, and a receiver, wherein the second receiving antenna is arranged outside the patient tunnel or in a vicinity of an opening of the patient tunnel, the method comprising:
receiving an interference signal by the receiver via the second receiving antenna;
receiving a magnetic resonance signal by the receiver via the first receiving antenna;
discarding the magnetic resonance signal as a function of the interference signal received by the second receiving antenna,
wherein the MRI scanner is configured to receive magnetic resonance signals having a Larmor frequency in an industrial band.

43. In a non-transitory computer-readable storage medium that stores instructions executable by a controller of an magnetic resonance imaging (MRI) scanner for operation of a magnetic resonance imaging (MRI) scanner, wherein the MRI scanner has a patient tunnel, a first receiving antenna for receiving a magnetic resonance signal from a patient in the patient tunnel, a second receiving antenna for receiving a signal close to the Larmor frequency of the magnetic resonance signal, and a receiver, wherein the second receiving antenna is arranged outside the patient tunnel or in a vicinity of an opening of the patient tunnel, the instructions comprising:
receiving a frequency portion of the interference signal close to the Larmor frequency by the receiver via the second receiving antenna;
receiving a magnetic resonance signal by the receiver via the first receiving antenna;
processing the magnetic resonance signal as a function of the frequency portion of the interference signal by the receiver to a receive signal, wherein a dependency is a function of a parameter; and
setting the parameter by the receiver, so that a portion of the interference signal is reduced in the receive signal,
wherein the MRI scanner is configured to receive magnetic resonance signals having a Larmor frequency in an industrial band.

* * * * *